US012595731B2

(12) United States Patent
Tucker et al.

(10) Patent No.: US 12,595,731 B2
(45) Date of Patent: Apr. 7, 2026

(54) USING MICROBIAL DNA IN WELL PLANNING AND MANAGEMENT

(71) Applicant: Oxy USA Inc, Houston, TX (US)

(72) Inventors: Yael Tarlovsky Tucker, The Woodlands, TX (US); Ayelet Blattstein Harris, Houston, TX (US)

(73) Assignee: Oxy USA Inc., Houston, TX (US)

( * ) Notice: Subject to any disclaimer, the term of this patent is extended or adjusted under 35 U.S.C. 154(b) by 528 days.

(21) Appl. No.: 18/170,297

(22) Filed: Feb. 16, 2023

(65) Prior Publication Data

US 2023/0279775 A1 Sep. 7, 2023

Related U.S. Application Data

(60) Provisional application No. 63/310,836, filed on Feb. 16, 2022.

(51) Int. Cl.
*E21B 49/08* (2006.01)
*C12Q 1/04* (2006.01)

(52) U.S. Cl.
CPC .............. *E21B 49/08* (2013.01); *C12Q 1/04* (2013.01)

(58) Field of Classification Search
CPC ................................. E21B 49/08; C12Q 1/04
See application file for complete search history.

(56) References Cited

U.S. PATENT DOCUMENTS

| | | |
|---|---|---|
| 8,141,633 B2 | 3/2012 | Hampton et al. |
| 8,666,667 B2 | 3/2014 | Michael et al. |
| 9,771,795 B2 | 9/2017 | Knight et al. |
| 10,330,659 B2 | 6/2019 | Dreyfus et al. |
| 10,585,078 B1 | 3/2020 | Liu et al. |

(Continued)

FOREIGN PATENT DOCUMENTS

| | | | | |
|---|---|---|---|---|
| WO | WO-2015103332 A2 | * | 7/2015 | ............. C12Q 1/689 |
| WO | WO-2018075701 A1 | * | 4/2018 | ............... C12Q 1/04 |

OTHER PUBLICATIONS

Zhang, Y., Dekas, A. E., Hawkins, A. J., Parada, A. E., Gorbatenko, O., Li, K., & Horne, R. N. (2020). Microbial community composition in deep-subsurface reservoir fluids reveals natural interwell connectivity. Water Resources Research, 56, e2019WR025916. https://doi.org/10.1029/2019WR025916 (Year: 2019).*

(Continued)

*Primary Examiner* — Catherine T. Rastovski
*Assistant Examiner* — Nyla Gavia
(74) *Attorney, Agent, or Firm* — Jackson Walker LLP; Leisa Talbert Peschel

(57) ABSTRACT

The present invention relates to systems and methods for well planning and management in a field to maximize the production of hydrocarbons. Specifically, the present invention involves identifying microbial compositions (including phenotypic microbial compositions) of solid samples, such as cuttings or core samples, or fluid samples, such as produced or injected fluids and determining well communication or fracture height (frac height). With well communication and/or frac height analysis using microbial compositions, the operator can better plan the placement and geometry of wells in a field to maximize production and reduce the number of wells that need to be drilled to maximize that production.

18 Claims, 9 Drawing Sheets

(56)                    References Cited

U.S. PATENT DOCUMENTS

| | | | |
|---|---|---|---|
| 10,760,418 B1 | 9/2020 | Liu et al. | |
| 10,767,476 B2 | 9/2020 | Knight et al. | |
| 10,975,691 B2 | 4/2021 | Knight et al. | |
| 11,028,449 B2 | 6/2021 | Knight et al. | |
| 11,047,232 B2 | 6/2021 | Knight et al. | |
| 2010/0243241 A1* | 9/2010 | Hampton | E21B 47/113 |
| | | | 340/856.4 |
| 2012/0053838 A1 | 3/2012 | Andrews et al. | |
| 2014/0116682 A1 | 5/2014 | Bracho Dominguez et al. | |
| 2017/0139078 A1 | 5/2017 | Knight et al. | |
| 2017/0370213 A1* | 12/2017 | Knight | E21B 47/11 |
| 2019/0316166 A1* | 10/2019 | Summers | E21B 43/16 |
| 2019/0390246 A1* | 12/2019 | Embree | A23K 10/16 |
| 2021/0010370 A1 | 1/2021 | Knight et al. | |
| 2021/0396135 A1 | 12/2021 | Knight et al. | |
| 2021/0404333 A1 | 12/2021 | Knight et al. | |

OTHER PUBLICATIONS

A. E. Pomerantz, G. T. Ventura, A. M. Mckenna, J.A. Canas, J. Auman, K. Koerner, D. Curry, R. K. Nelson, C.M. Reddy, R.P. Rodgers, A.G. Marshall, K.E. Peters, O.C. Mullins, "Combining biomarker and bulk compositional gradient analysis to assess reservoir connectivity", Organic Geochemistry, (Aug. 2010), pp. 812-821, vol. 41, Issue 8.

T. Matos, Written Opinion for International Patent Application No. PCT/US2023/013221, dated Jul. 6, 2023, United States Patent Office.

T. Matos, International Search Report for International Patent Application No. PCT/US2023/013221, dated Jul. 6, 2023, United States Patent Office.

Atlas, R. M., Bartha, R., Microbial Ecology: Fundamentals and Applications, 2nd Edition, (1987), 12 pages, Benjamin/Cummins Publishing Co., Menlo Park, CA.

Bastin, E.S., Greer, F.E., Merritt, C.A., Moulton, G., "The Presence of Sulphate Reducing Bacteria in Oil Field Waters", Science AAAS, Jan. 1, 1926, retrieved from https://www.jstor.org/stable/1649067, pp. 21-24, vol. 63, No. 1618, American Association for the Advancement of Science.

Bastin, E.S., Anderson, B., Greer, F.E., Merritt, C.A., Moulton, G., "The Problem of the Natural Reduction of Sulphates", Bull. Am. Proc. Petrol. Geol., (1926), pp. 1270-1299.

Colwell, R.R., "Genetic and Phenetic Classification of Bacteria", Advances in Applied Microbiology, (1973), pp. 137-175.

"Summary of Cost Associated with Seismic Data Acquisition and Processing", (Apr. 12, 2013), 1 page, Rev. 3.

Economides, M.J., Martin, T., "Modern Fracturing: Enhancing Natural Gas Production", Sep. 2007, 22 pages.

Valko, P., Economides, M.J., "Hydraulic Fracture Mechanics", John Wiley & Sons, (1995), 10 pages.

Economides, M.J., Wang, X., "Chapter 2 Natural Gas Production", (2007), 22 pages.

Gyllenberg, H.G., "Character correlations in certain taxonomic and ecologic groups of bacteria. A study based onf factor analysis", (1995), pp. 82-90, vol. 43, Iss. 2.

Loutit, M.W., Miles, J.A.R., "Microbial Ecology", Proceedings in Life Sciences, (1978), 27 pages, Springer-Verlag, Berlin.

Howard, G.C., Fast, C.R., "Hydraulic Fracturing", Society of Petroleum Engineers of AIME, (1970), 7 pages.

Hubbert, M.K, Willis, D.G., "Mechanics of Hydraulic Fracturing", Trans. AIME, (1957), 26 pages.

Langille, M.G., Zaneveld, J., Caporaso, J.G., Mcdonald, D., Knights, D., Reyes, J.A., Clemente, J.C., Burkepile, D.E., Vega Thurber, R.L., Knight, R., Beiko, R.G., Huttenhower, C., "Predictive functional profiling of microbial communities using 16S rRNA marker gene sequences", Nature Biotechnology, (Aug. 25, 2013), pp. 814-821, vol. 31, No. 9.

Nolte, K.G., "Determination of Fracture Parameters Using Nonlinear Regressing Analysis", Society of Petroleum Engineers 8341, (Sep. 1979), 16 pages.

Nolte, K.G., Smith, M.B., "Interpretation of Fracturing Pressures", Society of Petroleum Engineers, (Sep. 1981), 10 pages.

Robinson, J.A., "Determining Microbial Kinetic Parameters Using Nonlinear Regression Analysis", Advances in Microbial Ecology, (1985), pp. 61-114.

Rosswall, T., Kvillner, E., "Principal-Components and Factor Analysis for the Description of Microbial Populations", Advances in Microbial Ecology, (1978), pp. 1-48.

Sneath, P.H.A., Sokal, R.R., "Numerical Taxonomy: The Principles and Practice of Numerical Classification", (1973), 52 pages, W.H. Freeman and Company, San Francisco, United States.

Sokal, R.R., Rohlf, F.J., "Biometry: The Principles and Practice of Statistics in Biological Research", (1981), 19 pages, W.H. Freeman and Company, New York, United States.

Steel, R.G.D., Torrie, J.H., "Principles and Procedures of Statistics: A Biometrical Approach", (1960), 15 pages, McGraw-Hill Book Company, Inc.

Sundman, V., Gyllenberg, H.G., "Application of Factor Analysis in Microbiology: General Aspects on the Use of Factor Analysis in Microbiology", Annals of the Academy of Sciences of Finland Series A IV, (1967), pp. 1-32, vol. 112.

Sundman, V., "Four Bacterial Soil Populations Characterized and Compared by a Factor Analytical Method" Canadian Journal of Microbiology, (Nov. 5, 1969), retrieved from https://www.cdnsciencepub.com, pp. 455-464, vol. 16.

Sundman, V., "Description and Comparison of Microbial Populations in Ecological Studies with the Aid of Factor Analysis", Bulletins from the Ecological Research Committee, (1973), retrieved from https://www.jstor.org/stable/20111552, pp. 135-141, vol. 17.

Tucker, Y.T.. "Microbiology in Shale: Alternatives for Enhanced Gas Recovery", Graduate Theses, Dissertations, and Problem Reports 6834, (2015), retrieved from https://researchrepository.wvu.edu/etd/6834/, 105 pages.

Valko, P., Ecoomides, M.J., "Hydraulic Fracture Mechanics", (1995), 10 pages, John Wiley & Sons Ltd., New York, United States.

Williams, B.B., Gidley, J.L., Schechter, R.S., "Acidizing Fundamentals", Society of Petroleum Engineer of AIME, (1979), 8 pages.

\* cited by examiner

MICROBE POSITIONING

MICROBES CHANGE SIGNIFICANTLY

Vertically            Horizontally

CUTTINGS PROFILE

Cuttings Profile

Types of Microbes:

Hydrocarbon Degraders (Good)

Sulfur Reducing Bacteria

Corrosion Microbes

Regular Well

Pilot Well

Missing Information

0%   20%   40%   60%   80%   100%
10%   30%   50%   70%   90%

Avg(Value)

PRODUCED FLUIDS

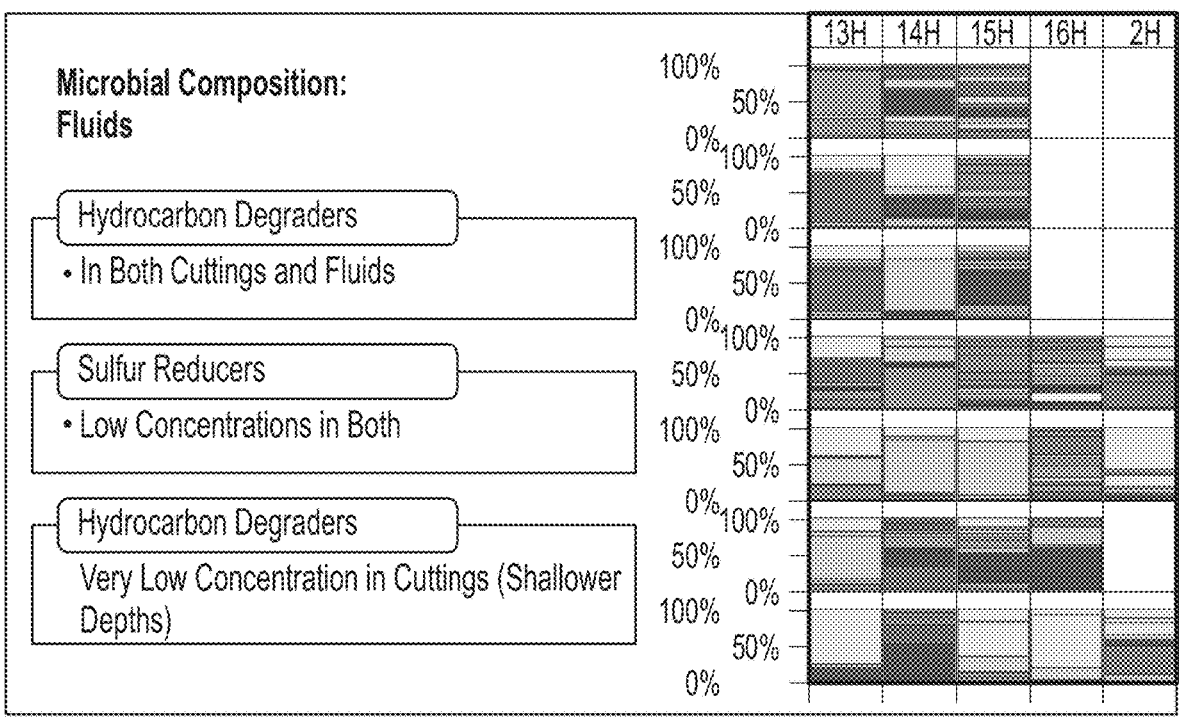

Microbial Composition:
Fluids

Hydrocarbon Degraders
• In Both Cuttings and Fluids

Sulfur Reducers
• Low Concentrations in Both

Hydrocarbon Degraders
Very Low Concentration in Cuttings (Shallower Depths)

FIG. 5

MICROBIAL COMPOSITION:

Microbial Composition:
Oil vs. Water

• Samples taken to See if Differences Could be Identified of Microbes in Each Fraction.
   • Oil vs. Produced Fluid (Water and Oil)
   • Some Differences did Exist
• Oil Signatures More Diverse in this Dataset

FIG. 6

WELL COMMUNICATION (LEAVE ONE OUT)

WELL COMMUNICATION (MICROBE ALLOCATION)

WELL COMMUNICATION (CHANGES OVER TIME)

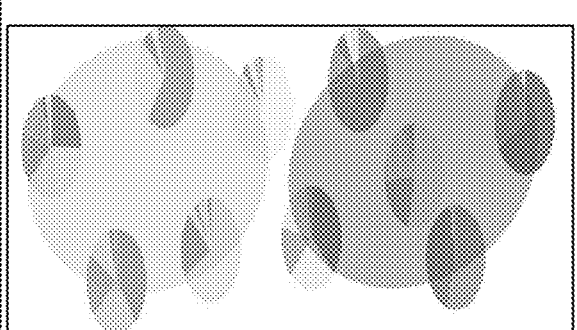 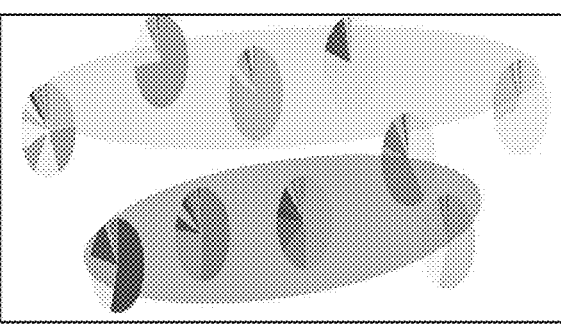

COMMUNICATION
CHANGES OVER
TIME

- After Gas Lift Install - Vertical Communication
  Appears to be Key

- After New Wells are Put Online and these
  Wells Experience Communication Paths
  Shift to Dominant Horizontal

FIG. 9

FRAC HEIGHT ALLOCATION OVER TIME

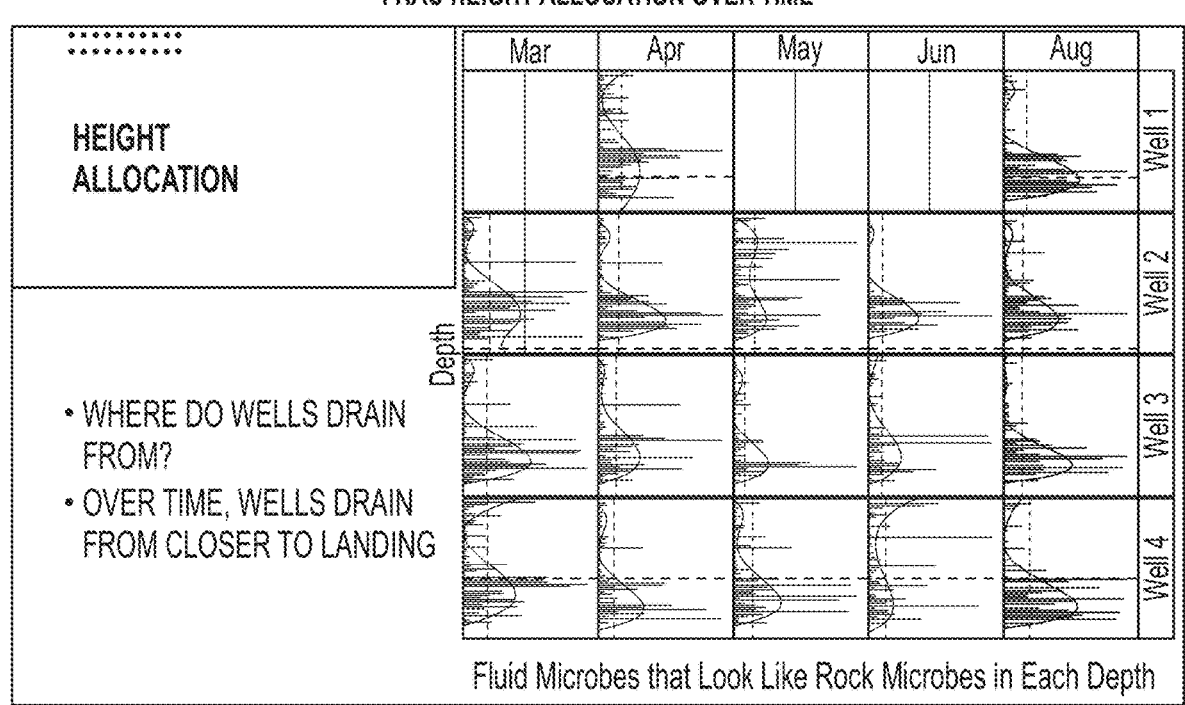

HEIGHT
ALLOCATION

- WHERE DO WELLS DRAIN
  FROM?
- OVER TIME, WELLS DRAIN
  FROM CLOSER TO LANDING

Fluid Microbes that Look Like Rock Microbes in Each Depth

FIG. 10

COMBINING PETROPHYSICAL DATA WITH MICROBIAL COMPOSITION ANALYSIS

USING MICROBIAL DNA IN WELL PLANNING AND MANAGEMENT

The present application claims the benefit of U.S. Provisional Application No. 63/310,386, filed Feb. 16, 2022, which is incorporated herein by reference in its entirety.

BACKGROUND OF THE INVENTION

A. Field of the Invention

The present invention relates to systems and methods for well planning and management. Specifically, the present invention relates to identification of microbial phenotypes in novel systems and methods for optimizing the production of hydrocarbons and/or water, including by determining well communication and fracture height (also referred to as frac height).

B. Background and Related Art

The objective of hydraulic fracturing oil and gas wells is to enhance the rate of hydrocarbon production to make the enterprise of acquiring, drilling, completing, and operating the well profitable. Rarely can hydrocarbons be accessed without providing a wellbore from the surface of the earth to some depth where subterranean rock formations may contain hydrocarbons. In addition to drilling a wellbore beneath the surface, it is often necessary to perform hydraulic fracturing to open pathways in the subterranean rock formations to enhance recovery of hydrocarbons.

Hydrocarbon production via a wellbore is constrained by the nature of the subterranean formation, whether the formation is classified as "reservoir rock" or "source rock." Assuming the subterranean formation contains ample quantities of hydrocarbons to allow for an economic enterprise to be had in its construction and operation, the wellbore represents the route by which hydrocarbons are transferred from the formation to the surface.

Wellbores are costly to construct and the cost increases with both the depth and the diameter of the drilled hole. The tendency, therefore, is to make the well no larger in diameter or deeper in depth than is necessary to make them economical over some period of productive time. While there may be a reduction in costs by reducing the number of vertical wellbores by drilling laterals, there is also a diminishing return aspect of making the lateral portion of horizontal wells longer.

Hydrocarbon flow from a subterranean formation to a vertical well is radial in nature, i.e., converging on the wellbore from three hundred and sixty degrees (360°). Like individuals entering a revolving door, the amount of oil or gas that can enter or exit at any point in time is limited. See FIG. 2.6 Configurations of Radial Flow and Fractured Vertical Well (Economides and Wang, 2007).

Successful hydraulic fracturing effectively increases the diameter of the wellbore (e.g., the revolving door) to permit greater volumes of hydrocarbons to be produced. Hydraulic fracturing achieves this by transitioning the flow regime in the formation from radial to linear, analogous to forming "aisles" to facilitate an exit from an otherwise crowded theatre filled with only seats. Successful hydraulic fracturing creates somewhat symmetrical and comparatively highly permeable "pathways" via a propped hydraulically induced fracture from some depth away from the wellbore into the formation. These hydraulically fractured pathways are created by administering a fracturing fluid capable of translating hydraulic pressure at the wellhead (on the surface) via the wellbore to the formation, initiating and extending one or more fractures from the wellbore into the formation. A proppant, such as sand, is often added to the fracturing fluid to form a slurry. It is this slurry that comprises the volume of the fracturing fluid which, in turn, relates to the volume of the hydraulically induced fracture.

Historically, in land-based operations, wells drilled to produce hydrocarbons have comprised of only a vertical section. The trajectory of the vertical wellbore was primarily perpendicular to the surface of the ground and along what is represented in FIG. 1 and FIG. 2 as the y-axis.

With the advent of offshore and unconventional well completions, wells drilled to produce hydrocarbons may have also comprised a section of the wellbore which curved away from the vertical wellbore to form a lateral or primarily horizontal portion of the well. This lateral or horizontal portion is represented here by changes along the x-axis in FIG. 1 and FIG. 2. The horizontal portion is more-or-less perpendicular to the vertical portion of the well and more-or-less parallel to the surface. In actual practice, the lateral/horizontal portion of the wellbore may undulate to follow elevation changes in the target formation, or it may be intentionally drilled in such a fashion as to have the angle of the horizontal increase in elevation along the path of the lateral so as to have the "toe" of the lateral at an elevation closer to the surface of the land (i.e., toe-up), or drilled downward so as to have the toe of the lateral at an elevation farther from the surface of the land (i.e., toe down.)

Hydraulic fractures emanate from the wellbore by the force of the fracturing fluid against the subterranean formation at the point where the well is perforated. It is not uncommon for hydraulic fracturing gradients to be as much as 0.95 psi/ft of depth, making the bottom hole fracturing pressure at the point of a perforation 8,000 ft. below the surface 7,600 psi. It is at or above this pressure that the fracturing fluid enters the perforation, contacts the formation, and initiates one or more fractures in the rock. In the examples shown in FIG. 1 and FIG. 2, such fractures emanate from the wellbore in the z-direction. The fracture volume increases with the addition of fracturing fluid, the width of the fracture enlarging during pumping as measured along the x-axis, the frac height changing in the y-direction, and the frac-length extending further from the wellbore in the z-direction. The direction in which the fractures extend their length from the wellbore is known as the azimuth. The number of fractures emanating from the wellbore may be more than one (1), and given differences in the nature of the rock and the relative stresses it is under, the azimuth may be different for each frac stage. Changes in frac height, frac length, and the azimuth of the hydraulically induced fracture may result in the frac communicating with another fractured stage in the same well, or even with another well. Changes in the frac height may result in the intended frac as originally designed communicating with zones or benches above or below the target bench.

Once the fracturing treatment is completed, much of the spent fracturing fluid (i.e., flowback) is recovered leaving the proppant to "prop open" the fracture and to form a highly permeable pathway from points deep in the subterranean formation to the wellbore. The highly permeable pathway, generally referred to as the proppant pack, is designed to be of sufficient strength to hold the hydraulic fracture open as well as to provide a permeability contrast between the formation and the propped fracture. It is this permeability contrast which facilitates flow from the formation to the propped fracture that effectively converts the flow regime in the formation from one of radial flow directly to the wellbore to one of a more orderly (possessing a more gradual pressure drop) linear flow to the wellbore.

Due to the very high cost of hydraulic fracturing relative to the cost of drilling and completing the well and giving consideration to the placement and number of subsequent wells to be completed in the same or proximate formations, knowledge of the geometry and dimensions of the hydraulically induced fracture are extremely important. Too few wells and the hydrocarbon resource is under-produced, perhaps even lost. Too many wells and the enterprise can quickly become uneconomical, as well as potentially resulting in a loss of hydrocarbon reserves.

Actual frac geometry is a consequence of hydraulic fracturing created by the volume of fracturing slurry applied, but the consequential created fracture volume is not easily discerned. In actuality, the newly created fracture volume may only be a fraction of total volume of fracturing fluid injected (Williams, Gidley, and Schechter, 1979, pg. 63; Valkó and Economides, Chapter 8: Material Balance), or, arguably, it may be a multiple of the injected volume (Schlumberger, 2014). The former may be the case where the formation possesses a leak-off capacity in excess of the fracturing fluid pump rate. The latter seems to be the case in highly stressed unconventional shale fracture treatments where microseismic assessments of the induced fractures often indicate a total frac volume different than the volume of the injected frac fluid. Such an array of possible fracture geometry responses serves to make the planning and design of fracture treatments more difficult.

In a hypothetical horizontal well fracturing treatment in the Permian Basin, for instance, in a well that has a true vertical depth (TVD) of approximately 8,000 feet and a lateral length of 10,000 feet, the "total" depth of the well might be approximately 20 to 22,000 feet, including the curved section. The well design might call for 50 to 60 separate frac stages, where the casing may be perforated at intervals of 150 to 300 feet, where each interval is isolated and fractured (also referred to herein as frac'd) individually. Each stage may be frac'd with 8,000 to 10,000 barrels of frac fluid, containing 300,000 to 500,000 pounds of sand, combined to form a fracturing fluid slurry ranging from 50,000 to 60,000 cubic feet. With approximately 50 to 60 stages, the entire well might require as much as 600,000 barrels of frac fluid and 15,000 tons of sand. Such wells are typically frac'd at 80 to 120 barrels per minute (BPM). Each stage may take from 1 to 1.5 hours to pump. With stage and well preparations that routinely occur between stages requiring another 1 to 1.5 hours, approximately 10 stages may be completed per day.

In addition, rarely is a single well completed and hydraulically frac'd by itself. Rather, a set of wells, often 3 to 6 wells, may be frac'd more or less simultaneously (e.g., zipper frac'd). Surface treating pressures are typically 6,500 to 8,500 pounds per square inch (psi) requiring total working power to range from 15,000 to 30,000 or more hydraulic horsepower (hhp) per stage.

As described above, a typical well requires something on the order of 600,000 bbls of liquid and 15,000 tons of sand to frac. The volume of fracturing slurry for that typical well would be approximately 3.6 million cu.ft. If one presumes the fracturing fluid is 100% efficient, if the height of the fracture during the pumping treatment is 500 feet, and the frac width while pumping is 1 inch (0.083 ft.), then the total for all frac lengths is calculated to be about 87,000 ft. As such a volume of fluid and sand is divided up amongst 50 or so individual stages along a horizontal section of the wellbore that may extend from 5,000 to 15,000 feet, and as each frac stage generates at least two wings extending from the wellbore in opposite directions away from the wellbore, taken together, these calculations suggest that the average hydraulically fractured distance from the wellbore is 870 feet, and an offset well would probably be placed no closer than 1800 to 2000 feet away to accommodate its 50 frac stages each generating a frac length of about 1600 feet.

However, if the fluid efficiency is only 70%, the width of the hydraulically induced fracture while pumping is only 0.125 ft, or the treated frac height is 600 feet, then the calculated frac length would be much less. Moreover, if there are multiple fracs emanating from the wellbore, or if the fracs form a dendritic pattern as they move away from the wellbore, then the calculated frac length would also be much less than the estimate. With an offset well 2000 feet away, there could be 1500 feet or more of undeveloped formation between the two wells.

Thus, ascertaining the geometry of the hydraulically created fracture (i.e., frac height and frac length) is important to efficient and economical well management. Frac length is the calculated function of fluid volume divided by the product of pumping width times frac height. Frac length may also be estimated from microseismic events recorded during the frac treatment. Frac slurry volume is easily determined by flow and weight measurements taken on the surface during the frac treatment. Frac volume itself may be estimated by correcting frac slurry volume for fluid leak-off during the frac treatment. Pumping width is a function of rock properties, attending geomechanical stresses at the fracture initiation point, the fracturing slurry properties, and the pressure exerted by the pumping rate, all of which have been the subject of intense study since the inception of hydraulic fracturing in the late 1940's. The "big unknown" in ascertaining the geometry of hydraulically induced fractures is frac height and finding frac height is complicated by the very nature of having a horizontal wellbore from which to determine it.

During the late 1940's and the early 1950's the inclination of a hydraulically induced fracture as being either horizontal to the surface, vertical to the surface, or at some degree of tilt between the two was a topic of debate by frac design engineers. The question was resolved by Hubbert and Willis in a paper presented in 1957. Fractures tend to be formed which are perpendicular to the least principal stress. Therefore, near the surface, fractures tend to be horizontal, whereas at some depth near and below 1000 meters, hydraulically induced fractures are nearly always vertical. (Howard and Fast, 1970, pg. 22; Valkó and Economides, 1995, pg. 58).

Historically, in vertical wells where the vertical section of the well's casing is perforated to facilitate hydraulic fracturing, created frac height is vertically inclined and parallel to the wellbore. Typically, measuring post hydraulic fracturing treatment frac height is performed by plying the fracturing fluid with radioactive tracers and then conducting gamma ray logging of the perforated zone to determine where the fracturing fluid entered the formation, thus providing a proxy for the created frac height. In horizontal wells where the fracturing treatment is conducted via a primarily horizontal wellbore, the created fracture is perpendicular to the well and the wellbore bisects the frac height. See FIG. 1. The developing frac height grows as more fracturing fluid volume is pumped into the formation and further moves out of view of the wellbore as it extends above and below the horizontal wellbore. The entire effort directed at ascertaining the created frac height is further compromised by the very nature of the stress profile in the oil-bearing formation benches which are the target of the horizontal well. Reservoirs are generally bounded by lithologic zones of high stress which aid in confining the hydraulically induced fracture to the hydrocarbon-rich reservoir between them. Formations which are the targets of extended-reach horizontal wells are generally shales or related nano-permeability formations which historically may have formed the boundaries for the fracs of vertical wells. It is nearly impossible to confine frac height to these highly stressed benches, and the tendency is for the frac to propagate out of zone to less-pressurized benches above and/or below the targeted bench.

Frac height can vary as a function of all the factors influencing frac width, with the additional attributes of being perpendicular to a horizontal wellbore (and therefore extending above and below and out of view from the wellbore). Compound this over the 50 or more stages in a typical horizontal well, and the importance of frac height becomes paramount in determining not only the appropriate frac slurry volumes with which to treat each stage and each well, but in the placement of other wells as well as in adjacent potentially productive formations above and/or below the current formation bench of interest.

There are several methods currently in use to ascertain post-hydraulic fracturing frac geometries, some of which are combinations of one or more distinct methods to lend confidence in height and length determinations. Methods such as the use of bottom-hole pressure gauges, microseismic, fiber optics, geochemical and geobiological methodologies are used to make frac geometry determinations. Of those methods, the use of pressure gauges is arguably the current gold standard by which such determinations are made.

Microseismic monitoring of hydraulic fracture treatments in horizontal wells is, however, the most widely used method. Microseismic monitoring is made concurrent with the frac treatment and the evaluation of microseismic data can begin almost as quickly as it is generated. In contrast, monitoring bottomhole pressures with pressure gauges, while capable of being conducted during a frac treatment (Nolte and Smith, 1981) are more typically done post-frac by measuring pressure decline over some period while the well is being produced (Nolte, 1979). Bottom-hole pressure measurements despite being the best available art, i.e., more reflective of the productive performance of the well and the most direct measurement of fluid flow possible from the surface looking into the subsurface conditions, has limitations that are temporal and require highly skilled interpretation, especially as the number of wells in the vicinity of the first well are increased. In addition, the equipment used to make bottom-hole pressure measurements is mechanical and therefore subject to breaking down or being lost downhole. Moreover, the cost of bottom-hole pressure measurements is high. There are, as well, limitations to the information provided by conducting a microseismic survey, not the least of which is the significant cost it adds to the total cost to complete the well. It is not unusual for microseismic services and evaluations to exceed $1,000,000 per well (DOE/ NETL-2014/1671).

For instance, in a horizontal well hydraulically frac'd in Reeves Co., Texas (Permian Basin) in 2014 in which 31 separate stages were treated with a total of 11.2 million gallons (267,000 bbls.) water and 9.346 million pounds of sand to create a slurry volume of 1.6 million cubic feet, the microseismic survey reported an average frac length of 965 feet and an average frac height of 516 feet. Microseismic length for the 31 stages ranged from 318 feet to 2,243 feet. Microseismic height for the 31 stages ranged from 258 feet to 833 feet.

Per stage frac fluid volumes averaged 361,700 gallons, ranging from a minimum of 330,000 gallons to a maximum of 463,000 gallons with a standard deviation of 27,700 gallons, representing 7.66% of the average. Even with this minimal degree of variability between stages, the variability in the resulting microseismic frac height was almost 4 times higher with a standard deviation of 152 feet, representing 29.5% of the average. While microseismic measurements appear to be quite precise given differences are reported within 1 foot, with frac heights ranging from 258 to 833 feet in this particular well that accuracy is questionable and a less costly and more reliable method of measuring frac height would be beneficial. Microseismic volume and microseismic stage length determinations may also provide some insight into the potential intrawell communication between stages once frac'd and for interwell communication between wells once completed.

Other methods for determining well communication and/ or frac height are known but they are often expensive, labor-intensive, and slow down drilling and production operations. For example, U.S. Pat. No. 8,666,667 to Gerald Michael and Olufemi Jokanola (issued Mar. 4, 2014 claiming priority to Provisional Application No. 61/352,145 filed Jun. 7, 2010) describes hydrocarbon production and allocation methods and systems by means of compositional and isotopic analysis wherein individual reservoir compartments contribute differing amounts of fluid to a commingled production stream. Specifically, U.S. Pat. No. 8,666,667 describes using a first wellbore's compositional and isotopic analysis to aid in an allocation determination in a second wellbore's commingled production of hydrocarbons sourced from multiple compartments following a stimulation treatment. The allocation method relies upon a mass-balance determination of carbon isotopes and the compositional fraction of one or more of the carbon-based components of each reservoir compartment. This method gives information about an entire formation rather than specific depths, thus providing only a more general view of the subsurface. In addition, this method relies exclusively on produced fluid samples that are only initially tied back to rock material to determine the "geochemical fingerprint" of the formation.

U.S. Pat. No. 10,330,659 to Dreyfus et al. (issued Jun. 25, 2019 claiming priority to a PCT application filed Nov. 9, 2012) describes a method for determining the location, size, and fluid composition of a subsurface hydrocarbon accumulation by analyzing fluid from a seep. That method requires determining a noble gas signature of a sample and at least one or more of determining a clumped isotope signature of the sample and characterizing the ecology of the sample. The method then integrates the signatures to determine information about the subsurface accumulation, such as the location, fluid type and quality, and volume of a subsurface hydrocarbon accumulation. One major problem of this method is the reliance on samples from seeps because the fluid may be contaminated by both surface contaminants and subsurface contaminants.

Other known methods and systems analyze the geochemistry of hydrocarbons in the pore spaces of or adsorbed in organic-rich rock samples, such as, but not limited to, drill cuttings and drill cores, e.g., U.S. Pat. Nos. 10,585,078 and 10,760,418 issued to Liu and Jiang. For example, one system comprises means for obtaining hydrocarbon from an organic-rich rock sample, such as, but not limited to, a shale core sample or drill cuttings, that enable measurement of geochemical fingerprints using various analysis tools such as comprehensive two-dimensional gas chromatography with mass spectrometry (GCxGC-MS), comprehensive two-dimensional liquid chromatography (LCxLC), gas chromatography with isotope ratio mass spectrometry (GC-IRMS), fluorescence spectrometry, and electromagnetic scattering spectroscopic measurement such as Raman spectroscopy. The samples obtained, preserved, and prepared to use in a geochemical analysis must be of high quality or the geochemical analysis will not provide reliable information. Hydrocarbon information obtained from extracted hydrocarbons may include the following: organic compound absolute concentration; organic compound absolute mass; organic compound relative concentration; organic compound relative mass; derived fluid properties (e.g., API gravity, viscosity, gas-oil ratio, and the like); elemental (e.g., sulfur, oxygen, boron) absolute concentration; elemental relative concentration; elemental absolute mass; elemental relative mass; and elemental isotopic ratios. That information is then used to calculate a group of subsurface reservoir characterization indices to provide reservoir rock permeability, fluid viscosity, water saturation, and oil saturation information to make an optimal landing zone decision. Geochemical analysis of oil samples from producing wells in a time sequence may allow calculations of production contribution from each of the end member zones. A particular limitation of this methodology is that it is restricted to an evaluation of only hydrocarbons and not the total fluid composition.

The geochemical approach comes at a very high per well cost and does not allow for any estimation of total fluid frac height. More precisely, known geochemical analysis methods neglect the considerable question of produced fluid contribution by each of the hydraulic frac'd stages if the frac height extends into formation benches above and/or below the targeted hydrocarbon-bearing formation in which porosity is primarily filled with water. Analyzing only the hydrocarbon constituent completely misses the contribution to potential water-bearing zones proximate to the hydrocarbon target.

Some groups have proposed sequencing the genetic composition of microorganisms in geologic formations or production fluids and using that data to compare microbial communities. However, using DNA sequences and computer-based statistical analyses as described in prior art methods results in large amounts of data with high levels of noise making it difficult to draw any useful comparisons.

Microorganisms (also referred to as microbes) were observed by microscope as early as 1665 by Robert Hooke who identified fungi and protozoa. Bacteria were first observed by Antonie van Leeuwenhoek in the 1680s. The presence of microbes in oilfield settings was observed by Bastin and his team in 1926 who reported on their investigation of microbes from 67 well head samples from California and Illinois oil wells. Subsequent investigation has sought to characterize microbial communities in and around oilfield operations, including previous attempts to characterize the microbes in subsurface formations several kilometers below the earth's surface. There is a high degree of variability in natural ecosystems and often heterogeneity of distribution of microbes within habitats. See Atlas and Barth, 1987. To properly characterize microbial communities in an uncontrolled environment (such as an oil field), it is important to control for as many sources of contaminating microbes (e.g., introduced by oilfield operations such as fracturing slurry) as possible and properly apply statistics to isolate the real data about microbes present in the formation from the noise and contaminating microbes.

Atlas and Bartha (1987) speak to the use of classical statistical methods as tools for determining microbe community compositions, including measurements of variability, hypothesis, and significance testing, as well as analysis of variance (ANOVA), correlation and regression, and cluster, factor, and principal component analyses (PCA), which is herein incorporated by reference. Statistical software packages may be used with computers to aid the analysis. Specific methods related to numerical taxonomy have been describe by Sneath and Sokal (1973), and Sokal and Rohlf (1981). Other references directly related to the applications of statistical methods to microbial work include Gyllenberg (1965), Sundman and Gyllenberg (1967), Sundman (1970), Colwell (1973), Sundman (1973), Holder-Franklin, et al. (1978), Roswall and Kvillner (1978), and Robinson (1985).

A previous study by Yael Tarlovsky Tucker (Tucker 2015) demonstrated that subsurface formations in the Marcellus Shale in the eastern U.S. could be uniquely identified based on their microbial compositions.

Knight, et al. (U.S. Pat. Nos. 9,771,795; 10,767,476; 10,975,691, 11,028,449; 11,047,232; and U.S. patent application No. 20210010370) of Biota Technology, Inc. described using genetic information contained in microbial DNA to identify operational taxonomic units (OTUs) to compare microbial communities from downhole samples. The comparison involved using predictive machine-learned models to predict hydrocarbons at various locations. The process of assimilating such a large amount of data had the distinct disadvantage of generating a very large amount of useless data (noise).

There is therefore a need for improved methods to characterize microbial communities, particularly as they relate to subsurface formations from which hydrocarbons are being produced. The present invention overcomes the limitations of prior art methods by analyzing microbial compositions in specific methods to determine frac height and/or well communication to assist in well planning and operations.

SUMMARY OF THE INVENTION

The following presents a simplified summary of the disclosure in order to provide a basic understanding of some aspects of the disclosure. This summary is not an exhaustive overview of the disclosure. Its sole purpose is to present some concepts in a simplified form as a prelude to the more detailed description that is discussed later.

The present disclosure presents systems and methods for well management, including wells used in the production of hydrocarbons and/or water. Specifically, the present disclosure discusses methods to identify microbial phenotypes (e.g., generate microbial compositions by phenotypes of samples) and use that identification to optimize production from a given well or set of wells. The phenotypic microbial composition of various samples may be used to determine well communication and/or determine frac height.

The present disclosure overcomes several major issues associated with current technologies. First, in order to gain a better understanding of frac height or well communication, the analysis of microbial compositions in samples is orders of magnitude less expensive than current methods that rely on pressure profile data. Second, current methods that sequence samples from production operations look at microbial composition on an individual microbe basis, which generates large amounts of noise, such that the data is useless, and those methods do not correct for operational effects or known confounding effects of outlier data in the way described herein to determine well communication or frac height.

The present disclosure discusses sampling systems and methods by which samples are taken from pilot wells or a wellbore (e.g., solid samples, such as core samples or cuttings, or fluids) and then processed for further analysis of the microbial composition.

The present disclosure also discusses ways for identifying the microbial composition of samples, including at a phenotypic level. This involves extracting DNA or RNA from samples, preferably 16S ribosomal DNA (rDNA), and then sequencing that DNA or RNA followed by analysis to determine the phenotypic types of microbes present in the sample.

The present disclosure discusses combining sampling with microbial composition analysis in order to determine well communication to manage existing wells and/or plan for drilling of additional wells in order to maximize production and minimize the number of wells needed to maximize production. Well placement or pressurization may be altered based on the known communication between wells in order to maximize the flow of hydrocarbons from the producing wells of a field.

The present disclosure also discusses combining sampling with microbial composition analysis to determine frac height, including in some embodiments determining how frac height changes over time. Well placement or pressurization may then be altered based on the calculated frac height or changes in frac height over time.

BRIEF DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

FIG. 5 illustrates the phenotypic microbial compositions of fluid samples from multiple wells.

FIG. 6 illustrates the differences in phenotypic microbial compositions of samples from oil and produced fluids.

FIG. 9 illustrates how well communication may change over time.

FIG. 10 illustrates how frac heights change over time.

10

Figure 13:
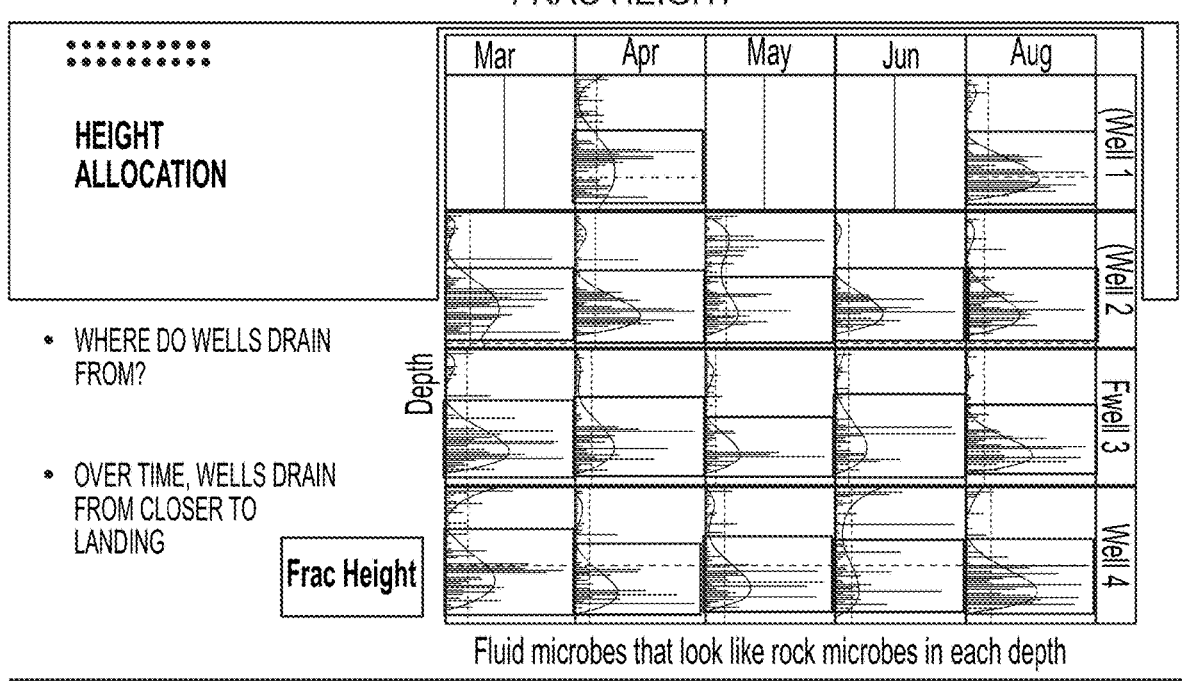

FIG. 13 illustrates how frac height is determined from polynomial fits to frac height data determined by microbial composition analysis for multiple wells.

DETAILED DESCRIPTION OF THE INVENTION

Illustrative embodiments of the disclosure are described below. In the interest of clarity, exemplary embodiments disclosed herein may not describe all features of an actual implementation. It will of course be appreciated that in the development of any such actual embodiment, numerous implementation-specific decisions must be made to achieve the producer's specific goals, such as compliance with environmental and business-related constraints, which will vary from one implementation to another. Moreover, it will be appreciated that such a development effort might be complex but would nevertheless be a routine undertaking for those of ordinary skill in the art having the benefit of this disclosure.

Disclosed herein are systems and methods for well management and planning. Specifically, these novel systems and methods relate to analyzing microbial compositions so as to optimize the production of hydrocarbons and/or water in a well or a set of wells, including by determining well communication and frac height.

The present invention can be embodied in various forms, including business processes, computer-implemented methods, computer program products, computer systems, and the like.

A. Definitions

As used in this disclosure, "a" or "an" may mean one or more. As used in the claim(s), when used in conjunction with the word "comprising," the words "a" or "an" may mean one or more than one.

"Drainage rock volume" refers to the volume of rock that has propped fractures and is contributing to production.

"Field," when used herein in reference to oil and gas operations, means a tract of land used for the purpose of extracting hydrocarbons, such as natural gas or crude oil, or water from the ground and/or used for the purpose of injecting water or gas.

"Landing" is the horizontal wellbore target in the formation. The depth of the landing may change at different stages or different positions in the same well in order to place the horizontal wellbore in the same stratigraphic formation, which is sometimes referred to as the target bench.

"Microbe" means microorganism. The microorganisms of greatest interest with respect to the methods disclosed herein fall within the bacteria and archaea domains.

"Phenotype" refers to one or more physical or biochemical characteristics of a microbe as determined by the interaction of its genetic constitution and the environment. For example, a phenotype of "sulfur-reducing bacteria" or "sulfur-reducing" refers to microbes (typically bacteria) who are able to reduce elemental sulfur to hydrogen sulfide.

"Phenotypic microbial composition" refers to the predicted compositional profile of microbes in a given sample by phenotype (i.e., relative abundances of phenotypes) and may contain some percentage of microbes that are not identified by phenotype (typically referred to as the unclassified fraction, which is preferably less than 10%). For example, a sample may have a phenotypic microbial composition of: 35% hydrocarbon degraders, 20% sulfur-reducing bacteria, 40% corrosion microbes, and 5% unclassified.

In addition to representation of a phenotypic microbial composition mathematically, such as with percentages to reflect the relative abundance of each phenotype, the phenotypic microbial composition may also be presented visually, such as in a pie chart. A "phenotypic microbial composition" is one type of a "microbial composition." A "microbial composition" also refers to a predicted compositional profile of microbes in a given sample by OTUs (i.e., relative abundances of OTUs).

"Set of wells" as used herein refers to two or more wells in a field. Analysis of a "set of wells" does not require analysis of every well in a field but may involve analysis of a subset of wells in the field. For example, an operator may have a field designated to have 100 total wells on it, but only have drilled twenty wells and is only analyzing a set of five of those wells to determine where to drill the next well in order to maximize production.

"Stimulated reservoir volume" refers to the volume of rock affected by fracturing activity.

B. Sampling

Samples for analysis may include solid samples, such as cuttings or core samples, or fluid samples. Fluid samples may include samples of produced fluid (fluid produced from the well after the well has been fractured), injected fluid, mud, or the like. Fluid samples may also be comprised of oil (or other hydrocarbons), water, or a combination of oil and water. These solid and fluid samples are taken in the field and if necessary, shipped on ice or dry ice for further analysis. After collection of the samples, DNA, preferably 16S ribosomal DNA (16S rDNA, which is approximately 1550 base pairs long and contains nine variable regions), is then chemically extracted from the samples and prepared for sequencing.

Figure 1:
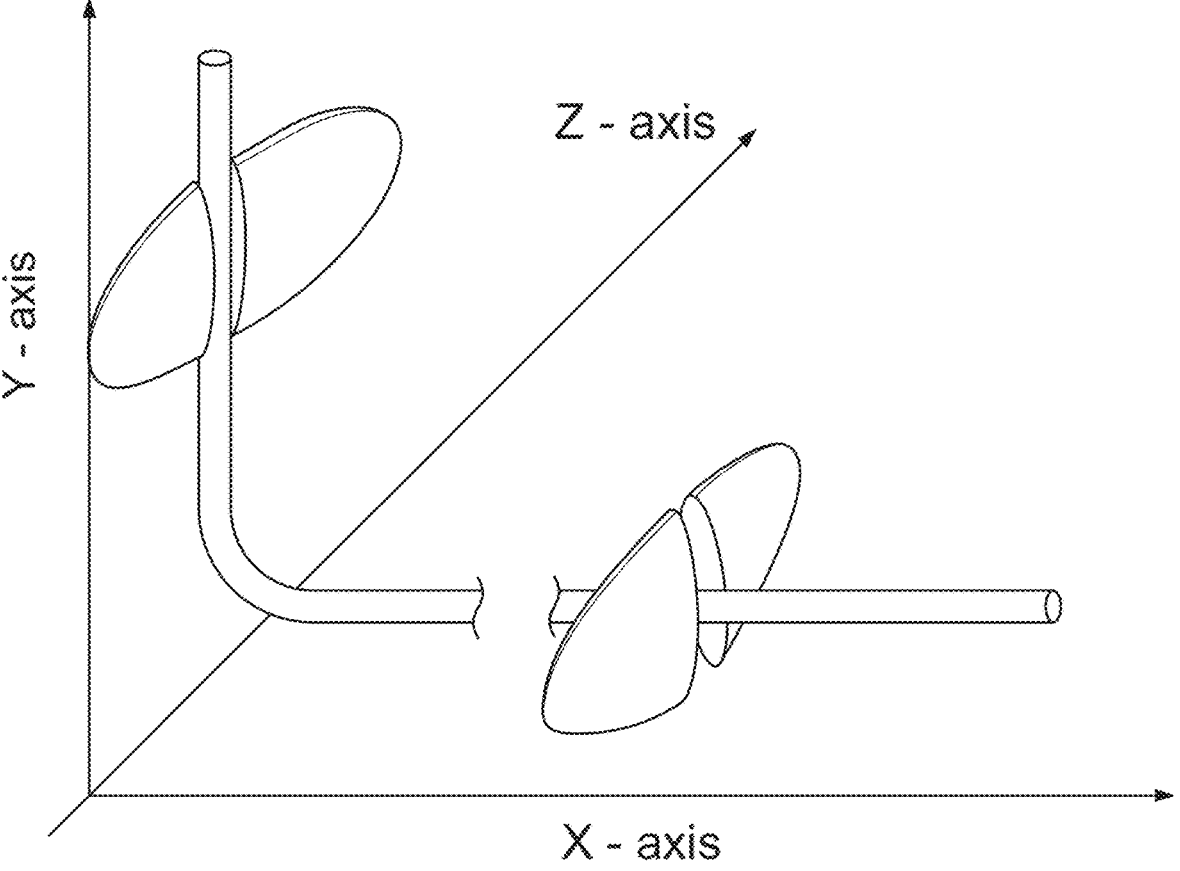
FIG. 1 illustrates a horizontal well and the concepts of frac height, frac width, and frac length.
Figure 2:
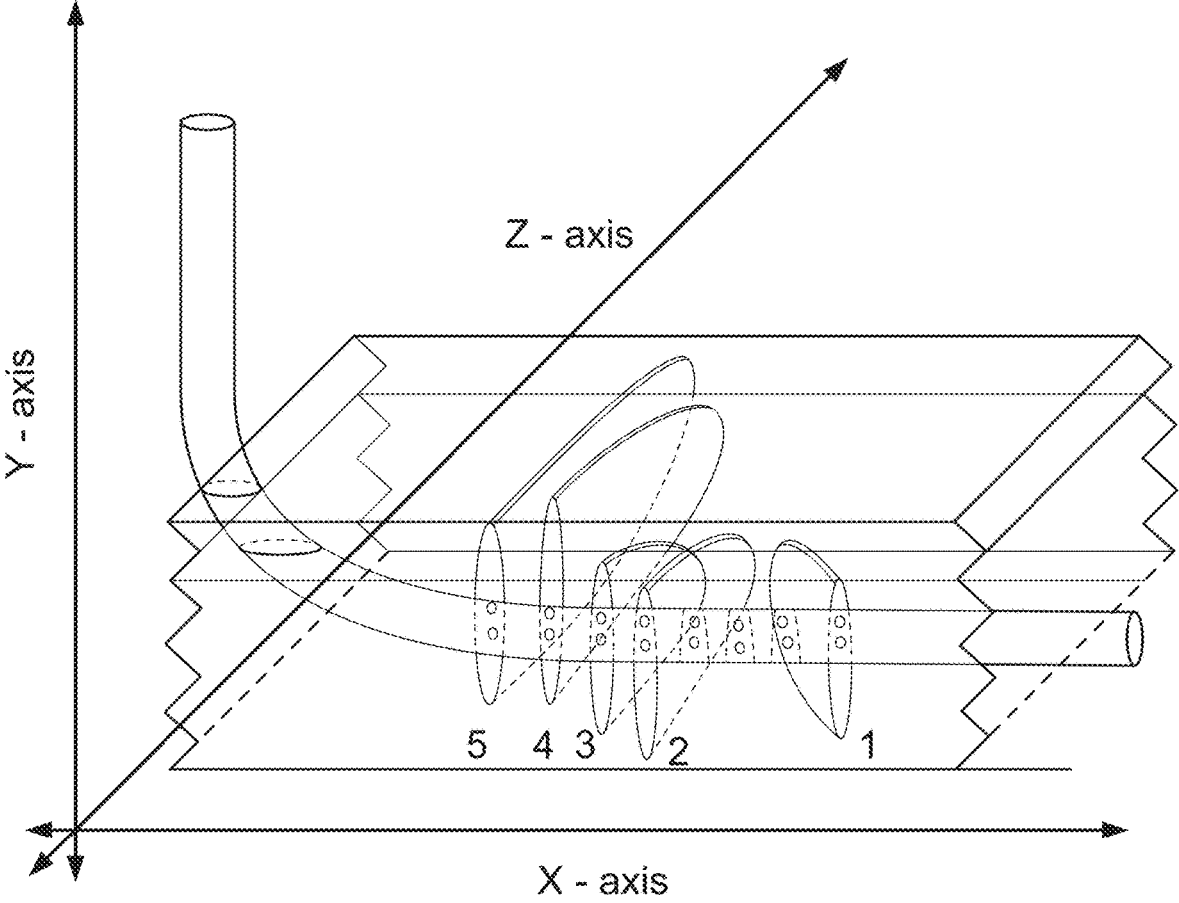
FIG. 2 illustrates the concept of frac azimuth and how that characteristic may be different for different stages of a well.
Figure 3:
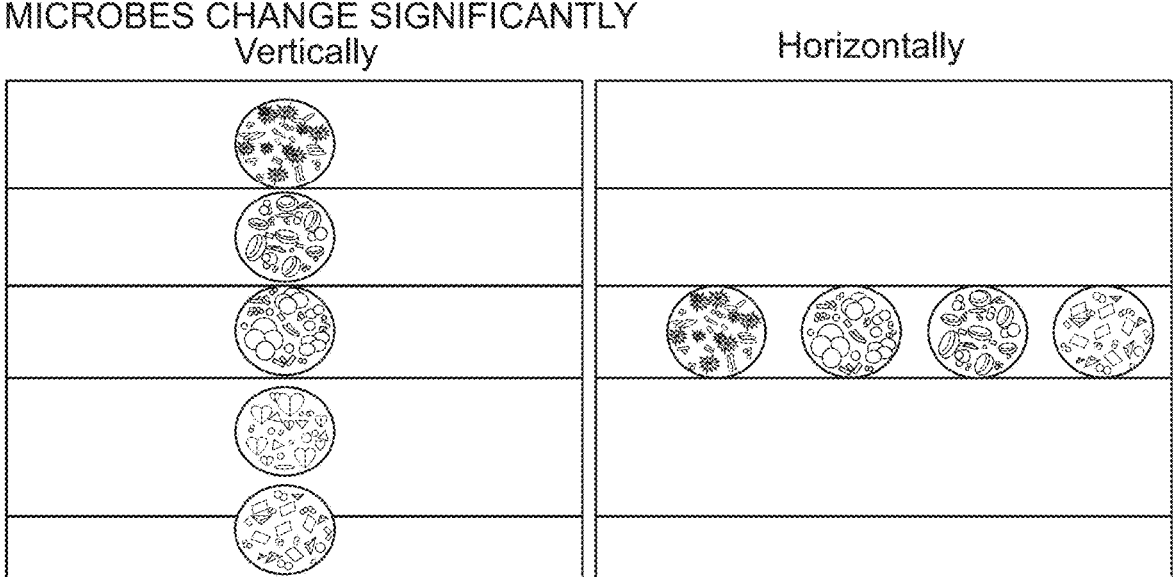
FIG. 3 illustrates that the compositions of microbes may be different in both horizontal and vertical directions of subsurface formations.

As shown in FIG. 3, below the surface, such as in a geologic formation, microbial compositions may be different in both vertical and horizontal directions. Microbial compositions may be used as a proxy to identify different zones or areas beneath the surface. As drilling and production operations occur near a particular zone or area, those operations may cause the microbial composition to change. For example, injection of fluid in a particular location may cause the migration of certain microbes into a zone or area they were not previously present. Likewise, mechanical disruption caused by drilling activities may cause changes to the microbial composition of a particular zone or area (including at particular wells or well locations). Thus, identifying the microbial compositions of particular zones or areas and how those microbial compositions, particularly phenotypic microbial compositions, change over time may provide valuable insight into what is happening beneath the surface.

To determine microbial composition, it is necessary first to collect relevant samples, including from beneath the surface. One type of below surface solid sample that may provide valuable information is a core sample. One of skill in the art understands how to take a core sample. Briefly, cylindrically shaped tubes are pushed or drilled down deep into the ground. When those tubes are pulled back up to the surface, they contain a core sample of the rocks and other materials below at known depths.

Another type of below surface solid sample is cuttings. Cuttings are broken bits of solid material removed from a drilled borehole and brought to the surface in the drilling mud or drilling fluid. The cuttings are produced as the rock is broken by the drill bit advancing through the rock or soil.

Cuttings may be separated from the drilling mud or fluid by mechanical means, including through use of shale shakers or centrifuges. After separation, cuttings may be rinsed with sterile water prior to further processing, In the field, core samples or cuttings may be collected into sterile sample bags (e.g., 118 ml capacity sterile bags 7.5 cm by 18.5 cm) or sterile tubes (e.g., 50 ml conical centrifuge tubes made from polypropylene (PP)/high density polyethylene (HDPE) that are non-pyrogenic, non-cytotoxic, DNase/RNase-free, and human DNA free) and kept on ice or in a freezer until DNA or RNA is extracted or such samples are shipped to another location for such extraction. For both cuttings and core samples, the sample bags or tubes may be filled to the fill line and preferably include the largest chunks of rock present within the interval being sampled.

Commercially available kits may be used to isolate (i.e., extract) DNA or RNA from solid samples, such as the MoBio PowerSoil® DNA Isolation Kit. To use for extraction, any solid samples need to first be milled (i.e., ground up). Any grinder or milling machine (e.g., the Bel-Art Micro-Mill II Grinder with stainless steel blade) that is able to pulverize rock may be used; however, it is important to sanitize the equipment to prevent cross-contamination such as by using ethanol or bleach between samples. Only a small amount of each sample is necessary for extraction, typically 0.25 grams, 0.5 grams, or 1 gram of sample is used.

Ideally, solid samples (i.e., core samples and cutting samples) are taken from multiple depths in order to collect data regarding microbial compositions of multiple zones or areas below the surface. For example, solid samples may be taken every 30 feet within a pilot well or wellbore. When solid samples are taken from a pilot well, it is preferable that the pilot well be located within 1000 to 1500 feet of the well of interest; however, the pilot well may be located anywhere from 10 feet to 79,200 feet (15 miles) from the well of interest. The known geology of a subsurface formation may influence the distance of the pilot well from one or more wells of interest. For example, if the subsurface formation is suspected to be fairly uniform in geology in the horizontal direction, the distance between the pilot well and well of interest may be larger (i.e., at or near the upper limit of the range) than if the geology is known to change dramatically within a smaller distance from the well of interest. If the subsurface geology is unknown or not characterized well, a pilot well within 10 to 1500 feet from the well of interest should be used.

The frequency at which solid samples are taken is preferably every 30 to 50 feet from the well (whether in the pilot well or a well of interest) but useful information can be recovered with sampling up to every 100 feet or up to every 250 feet. Sampling is possible every 10 feet and can provide greater resolution of changes in phenotypic microbial compositions; however, to sample at a frequency of every 10 feet usually requires that drilling be slowed down, which increases the cost of operations.

In some situations, there may be a particular depth of interest and therefore the depth sampling may occur in a subset of the entire depth of the well. For example, in determining whether there is water influx into the well, one may sample cuttings at 3000 feet below the surface and then every 100 feet up to the surface. As another example, the zone of horizontal drilling may be of particular importance and therefore a pilot well is sampled every thirty feet for 500 feet above and 500 feet below the depth of the horizontal bore.

In addition to the solid samples (i.e., core samples and cutting samples) discussed above, samples may also be taken from fluids. This may include fluid samples both before and after entry into a formation. For example, it may be beneficial to determine the microbial composition of drilling fluid before and after injection in order to determine if the drilling operation itself is introducing any microbes into the formation that may not be naturally present. Oil/water samples may also be preferably taken from the wellhead (or as close to the wellhead as possible). Fluid samples may also be collected from produced water held in storage tanks or from separators located at each well, preferably at the inlet of the separator.

For any fluid sampling, sterile tubes or bottles (e.g., 50 ml conical centrifuge tubes made from polypropylene (PP)/high density polyethylene (HDPE) that are non-pyrogenic, non-cytotoxic, DNase/RNase-free, and human DNA free) may be used for collection. As with the solid samples, once fluid samples are collected, they may be kept on ice or in a freezer until DNA is extracted from the sample. For extraction from fluid samples, the fluid may be first filtered using 0.22 μm filters, followed by extraction using commercially available kits such as the MoBio PowerSoil DNA Extraction kit using its standard protocol. Once DNA is extracted by elution into nuclease-free fluid, it may be frozen at −20° C. if sequencing does not occur immediately.

C. Microbial Compositions and Phenotypic Microbial Compositions

The microbial composition analysis begins with taking the extracted DNA from the samples and sequencing it. Many methods of DNA/RNA sequencing are currently known and would be available to those of skill in the art. In the preferred method, the extracted DNA is sequenced using next generation sequencing methods, where the sequencer copies the DNA using nucleotides (A, C, T or U, and G) that fluoresce when added. By monitoring the fluorescence, the sequencer records the sequence of nucleotides added.

For example, 16S rDNA of the samples is sequenced as follows. See Illumina 16S Metagenomic Library Prep Guide (Part #15044223 Rev. B), which is herein incorporated by reference. Briefly, primers with overhang adaptors are used to amplify the V3 and/or V4 region of the 16S rDNA of the samples. Then, indices and sequencing adaptors are attached and then the amplified products are sequenced on an Illumina MiSeq (Illumina, USA).

In a specific embodiment, 16S rDNA gene V4 variable region polymerase chain reaction primers 515 (GTGYCAGCMGCCGCGGTAA) and 806 (GGACTACNVGGGTWTCTAAT) may be used to amplify the V4 region for sequencing and include a barcode on the forward primer. Amplification uses PCR with the HotStarTaq Plus Master Mix Kit (Qiagen, USA) under the following conditions: 94° C. for 3 minutes; 28 cycles of 94° C. for 30 seconds, 53° C. for 40 seconds, 72° C. for 1 minute; and a final elongation step at 72° C. for 5 minutes. Samples are pooled and purified using calibrated AMPure XP beads (AMPure XP for PCR Purification Kit, Beckman Coulter, USA). The purified polymerase chain reaction (PCR) products are then used to prepare a nucleic acid library with adapters by following the Illumina TruSeq DNA library preparation protocol (Illumina, San Diego, California), which is herein incorporated by reference. The library is then loaded into a flow cell where fragments are captured on a lawn of surface-bound oligonucleotides complementary to the library adapters. Each fragment is then amplified into distinct, clonal clusters. When cluster generation is complete, the templates are ready for sequencing, which may be performed on a next generation sequencing machine such as the Illumina MiSeq (Illumina, USA). With specific reference to the Illumina sequencing method, such sequence-by-synthesis technology uses a reversible terminator-based method that detects single bases as they are incorporated into DNA template strands. Thus, each base (A, C, T, or G) is detected as the DNA is synthesized.

When samples are pooled and sequenced together, the initial sequencing results from a next generation sequencing machine may be presented in one or more FASTQ data files. A FASTQ data file is a text file that contains sequence (as well as base call quality score) data from clusters that pass a filter on a flow cell during the sequencing process. The first step in analyzing that data is to demultiplex the data by assigning each cluster to a specific sample based on the cluster's index sequence (e.g., the barcode added in library formation). The result of this demultiplexing is a set of raw sequences by sample.

The raw sequences of the samples (i.e., the specific sequences of A, C, T, G) may be further analyzed via commercially available software such as CLC Workbench (Qiagen, USA) or other software that aligns the sample sequences with known microbial sequences. The result of such analysis is typically an OTU Table. OTU stands for operational taxonomic unit. A taxonomic classification could also be made using the Metagenomics workflow (which uses the Greengenes database) available on the MiSeq Reporter (on-system software for the Illumina MiSeq) or available on BaseSpace (cloud-based software). Typically, a 97% homology level is used as a setting for assigning OTUs, however the homology level could be set at 90%, 91%, 92%, 93%, 94%, 95%, 96%, 97%, 98%, 99%, or 100%.

Merely knowing the raw sequences of samples or even the OTU Table is not useful in a practical sense because the sheer volume of data makes it difficult to draw useful conclusions. For example, there may be thousands of different microbes identified by sequencing per sample. It is not necessary to understand the thousands of differences in microbe compositions among samples in order to draw conclusions about well communication and frac height. A more useful application is to further analyze the sequences to generate a phenotypic microbial composition for each sample. A phenotypic microbial composition looks at the relative abundances by phenotype in a given sample and may include an unclassified portion. There are multiple publicly available software programs that may be used to convert sequencing data or OTU Tables into phenotypes from which phenotypic microbial compositions may be determined as discussed herein.

For example, PICRUSt (phylogenetic investigation of communities by reconstruction of unobserved states) may be used to estimate the phenotypic microbial composition. See Langille et al., "Predictive functional profiling of microbial communities using 16S rRNA marker gene sequences," Nature Biotechnology 31 (9), September 2013, which is hereby incorporated by reference for its description of PICRUSt and http://picrust.github.io/picrust2 (where PICRUSt, currently version 2, may be downloaded). Briefly, PICRUSt is a bioinformatics software package that predicts the functional composition of a microbial community's metagenome from its 16S sequencing data. The modeling algorithms of PICRUSt use 16S sequencing data and a reference genome database to predict the phenotypes of the microbes present. Typically, a user provides an OTU Table that includes OTUs for each sample with associated Greengenes identifiers as the input into PICRUSt. The correlation of OTUs to Greengenes identifiers may be determined using publicly available software such as QIIME (quantitative insights into microbial ecology, see Caporaso et al., "QIIME allows analysis of high-throughput community sequencing data." Nature Methods 7, 335-336, 2010) or CLC Work-bench (Qiagen, USA). If sequence denoising methods are used, the initial input may be amplicon sequence variants (ASVs) rather than OTUs. The second version of PICRUSt (PICRUSt2) is compatible with using either ASVs or OTUs. The default genome database in PICRUSt2 is based on 41,926 bacterial and archaeal genomes from the IMG data-base.

The output of a PICRUSt analysis is a metagenome table (i.e., counts of gene families on a per-sample basis). PICRUSt may also be used generate predictions for 41 microbial phenotypes (linked to the IMG genomes of the reference database). Of the 41 microbial phenotypes that can be predicted, the following are phenotypes especially rel-evant to the systems and methods disclosed herein: hydro-carbon degraders, sulfur-reducing bacteria, *Halanaerobium* sp. (known to contribute to acid production, thiosulfate reduction, and biofilm formation), acid producers, deferrib-acter (iron-reducing bacteria), and corrosion microbes. Although some of these phenotypes may use a genus name, the name is merely a shorthand way of grouping microbes that exhibit similar biochemical characteristics. For example, the phenotype *Halanaerobium* sp. may include bacteria within the genus *Halanaerobium* sp. but as used herein, "*Halanaerobium* sp." is a phenotype classification for microbes known to contribute to acid production, thio-sulfate reduction, and biofilm formation.

PICRUSt data may be used to determine the relative abundances of each phenotype present in a given sample and prepare an overall assessment of the phenotypic microbial composition for a given sample. For example, the pheno-typic microbial composition of a particular sample may be: 35% hydrocarbon degraders, 20% sulfur-reducing bacteria, 40% corrosion microbes, and 5% unclassified.

Another example of publicly-available software that can convert OTU Tables into functional profiles (phenotypes) is FAPROTAX (Functional Annotation of Prokaryotic Taxa, see https://pages_uoregon_edu/slouca/LoucalLab/archive/FAPROTAX/lib/php/indes.php). These include phenotypes grouping microbes that can perform methanogenesis, metha-nol oxidation, methylotrophy, ammonia oxidation, nitrite oxidation, nitrification, sulfate respiration, sulfur respiration, sulfite oxidation, sulfite respiration, thiosulfate respiration, arsenate detoxification, arsenate respiration, arsenite oxida-tion and detoxification, nitrate denitrification, nitrite deni-trification, nitrous oxide denitrification, denitrification, chi-tinolysis, nitrogen fixation, nitrate ammonification, nitrite ammonification, nitrite respiration, cellulolysis, xylanolysis, manganese oxidation, manganese respiration, ligninolysis, fermentation, and aerobic chemoheterotrophy, among oth-ers.

Alternatively, OTUs may be transformed into phenotypes relevant to well management and planning such as by applying the rules set forth in Table 1.

TABLE 1

| If the Taxonomic Classification is: | Classify as (Phenotype) |
|---|---|
| f_Acetobacteraceae | Acid Producing |
| g_Deferribacter | Microbial Induced Corrosion/ Iron Reducing Bacteria/ Nitrate Reducing Bacteria |
| g_Desulfotignum | H2S Producing |

16

TABLE 1-continued

| If the Taxonomic Classification is: | Classify as (Phenotype) |
|---|---|
| g_Desulfotomaculum | H2S Producing |
| g_Desulfovirgula | H2S Producing |
| g_Desulfovermiculus | H2S Producing |
| g_Desulfovibrio | H2S Producing |
| o_Desulfobacterales | H2S Producing |
| g_Desulfuromonas | H2S Producing |
| o_Methanobacteriales | Methane producing |
| o_Methanomicrobiales | Methane producing |
| o_Methanosarcinales | Methane producing |
| o_Methanomassiliicoccales | Methane producing |
| o_Methanococcales | Methane producing |
| o_Thermotogales | H2S Producing |
| g_Thermovirga | H2S Producing/Acid Producing |
| f_Halanaerobiaceae | H2S Producing/Acid Producing |
| f_Shewanellaceae | Microbial Induced Corrosion/ Iron Reducing Bacteria/ H2S Producing |
| g_Deinococcus | Radiation Resistant |

Table 1 provides specific examples of titles for pheno-types that may be relevant to drilling and production opera-tions, however, the critical aspect is not the name given for the phenotype itself, but rather characterizing microbes present by phenotype in order to reduce an enormously large data set into a smaller set of more relevant data. One of skill in the art could implement the rules identified in Table 1 by programming a computer to automatically convert the OTU or microbe name into the phenotypes listed according to the rules in Table 1. If implementing a set of phenotypic rules such as is shown in Table 1, one of skill in the art could also designate everything to which a rule does not apply as "unclassified." As discussed herein, not every microbe in a sample needs to be identified or classified by phenotype in order to be able to identify differences in phenotypic micro-bial compositions between samples.

Figure 4:
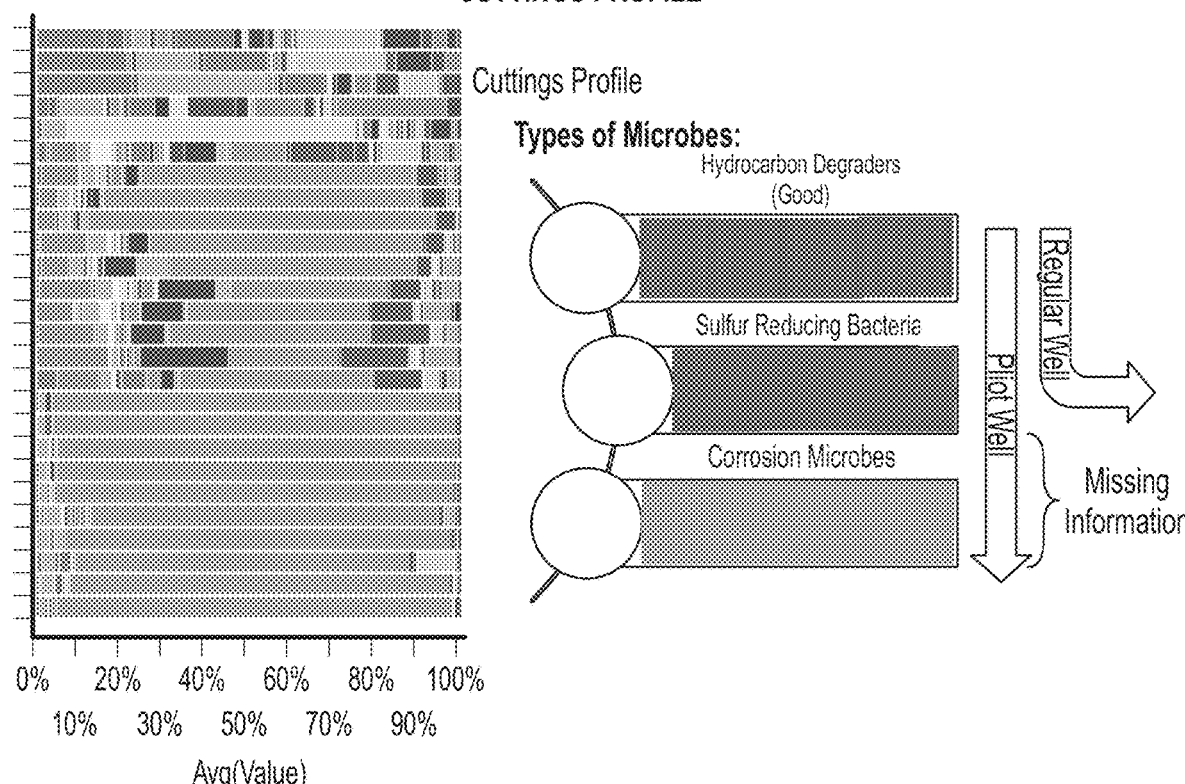
FIG. 4 illustrates the phenotypic microbial compositions of cuttings samples taken in a pilot well.

FIG. 4 illustrates one way to represent phenotypic micro-bial compositions of cuttings samples taken from a pilot well. As shown on the right, if solid samples are taken only from the "regular well," information concerning the micro-bial compositions in the zones or areas in which fracturing would occur, particularly that below the horizontal section of the wellbore, would be missing. By sampling cuttings from a nearby pilot well, additional relevant data may be collected. In this example, major relevant phenotypes pres-ent in these samples are hydrocarbon degraders, sulfur-reducing bacteria, and corrosion microbes. The graph on the left illustrates the phenotypic microbial compositions of cuttings samples by sampling depth. Each row represents an individual sample and the rows are arranged by depth. Thus, from a visual perspective, the graph shows how the pheno-typic microbial compositions change from the top to the bottom of the pilot well. As shown, corrosion microbes represent a much larger proportion and sulfur-reducing bacteria represent a much smaller proportion of the pheno-typic microbial compositions as the depth down the pilot well increases. In addition, FIG. 4 shows in this example that hydrocarbon degraders are present in higher proportions near the top of the pilot well and much lower proportions as the depth of the pilot well increases.

FIG. 5 illustrates phenotypic microbial compositions of fluid samples taken from multiple wells (e.g., 13H, 14H, 15H, 16H, and 2H) at multiple depths (illustrated in the graph on the right by each row representing a different depth). In this example, the phenotypes of major interest were hydrocarbon degraders, sulfur reducers (i.e., sulfur-reducing bacteria), and acid producing microbes. The graph on the right illustrates that each well contains a unique phenotypic microbial composition that changes by the depth sampled.

FIG. 6 illustrates differences in phenotypic microbial compositions of samples from oil and produced fluid (containing water and oil). As illustrated in the example represented in FIG. 6, the phenotypic microbial compositions of the oil samples were more diverse than the produced water samples. The graph on the right shows data for three wells and for each set shows the phenotypic microbial composition for the oil sample on the left and the phenotypic microbial composition for the produced fluid sample from the same well on the right. While there are microorganisms in common in both samples one can distinguish differences between the oil and water samples. The ability to distinguish the microorganisms associated with oil or water one can differentiate the fluid contribution which may be quite different because oil contribution to a well could be more or less (usually the case) confined than water. Without such a separation, the analysis is looking at total fluid and will therefore show a much larger contribution range than expected solely by oil. By running separate samples, one can begin to distinguish the unique water and oil (hydrocarbon) contribution to frac heights.

D. Well Communication

Well communication refers to whether two or more wells are producing from the same reservoir (whether of oil, other hydrocarbons, or water) and is indicative of connectivity between the wells. Well communication may change over time, particularly when there is active drilling and/or production activities near the wells of interest. For example, as fracturing operations occur, additional fractures in the geographic formations may open up new pathways for communication between wells (e.g., pathways by which fluid may flow from one well to another). Current methods for understanding well communication typically involve pressure profile data, which can cost up to 100 times the cost of microbial composition analysis.

Microbial composition analysis may help illuminate what pathways exist between wells. The more the microbe compositions of produced fluids from two wells begins to look like each other, the greater probability that those two wells are communicating because a pathway for the flow of material and/or fluid has opened up between them. By observing changes to microbial composition over time, either qualitatively or quantitatively, one can identify how fracturing operations, changes in production and/or other drilling activities have changed well communication. In addition, one of skill in the art can use the microbial composition analysis, including changes over time, to predict the impact of a new well on communication and/or production, to alter the pressurization of wells in the field to generate fractures in a specific geographic location to optimize production, or to minimize communication between specific wells.

Physics dictates that fluid will flow from an area of more pressure to an area of lower pressure. Thus, one of skill in the art understands how to apply pressure to direct fluid flow. In drilling operations, fracturing involves over pressurizing so as to break the rock and generate new fluid communication paths. For a given set of wells, the order of fracturing wells may impact well communication. By pressurizing nearby wells before fracturing operations (or shutting in a well to allow pressure to build), one of skill in the art can create conditions so that fractures develop in the opposite direction, which may be the predicted direction to tap into a reservoir of hydrocarbons. Optimizing production also involves de-pressurization methods. Production from a well releases pressure, thus allowing fluid flow to the surface. Gas lifts may also be used to release pressure in a given area.

In hydrocarbon production operations, it is preferable to avoid communications between wells that are producing hydrocarbons and wells that produce water because such communication reduces the rate at which hydrocarbons can be produced. Without an understanding of well communication paths, the typical pressurization and de-pressurization methods become essentially guesses as to how to best optimize production.

By adding a microbial composition analysis of well communication (preferably, involving phenotypic microbial composition analysis), operators may better understand well communication pathways and be able to better plan what pressurization and de-pressurization methods to use and when to use those methods in order to optimize production from a reservoir. Notably, operators do not have to turn off wells to change a drilling strategy in a field because relevant information may be provided by phenotypic microbial composition analyses during operations.

As described below, a microbial composition analysis that identifies the source of microbes for each well may be used to determine which wells are likely in communication. However, there may be an "unknown" fraction of microbes present in a given well that is unlikely to have been sourced from any other well. That unknown fraction may be extremely valuable in well management methods because wells with large unknown fractions may be initially identified as unique. As time goes on, those "unique" wells may start to look, in terms of microbial composition, like one or more other wells, which suggests that communication pathways have opened up between the wells whose microbial compositions now look similar.

Once samples have been taken and analyzed for microbial composition, SourceTracker software (or other software with the same functionality) may be used in a method to determine well communication. In particular, the software applies Bayesian statistics in a "leave one out" method by which probabilities for the source of microbes (whether identified individually or by phenotypes) are calculated by leaving out the data for one well at a time. The phenotypic microbial compositions of each sample are used as an input, along with whether each sample should be considered a "source" or a "sink." When determining well communication, each solid sample (to the extent used), such as a core sample or cuttings, is typically identified as a source, each produced fluid sample is identified as a source, and each injected fluid or mud sample is identified as a source. Typically, SourceTracker software requires two inputs: (i) a table of OTUs or the phenotypic microbial compositions per sample (identified by name); and (ii) a mapping file that includes the name of the sample and whether each sample is considered a source or sink. If a table of OTUs is used as an input to SourceTracker, Greengenes identifiers are included in the table. If a table of phenotypic microbial compositions is used as the input to SourceTracker (or other equivalent software to perform similar statistics, such as Bayesian statistics), then a unique identifier should be used for each phenotype. The mapping file may include other data related to the sample but that data is not used by SourceTracker. When cuttings or core samples are used for controls in a well communication analysis, one may identify the name of those samples to SourceTracker as formation and that each is a source in the input mapping file. In that case, the output would identify anything coming from the formation as formation, which controls for the influence on well communication of the same microbes coming from the same rock. For fluid samples, the name on the input mapping file may include an indicator of the depth the sample was taken, and each sample is identified as a source.

Figure 7:
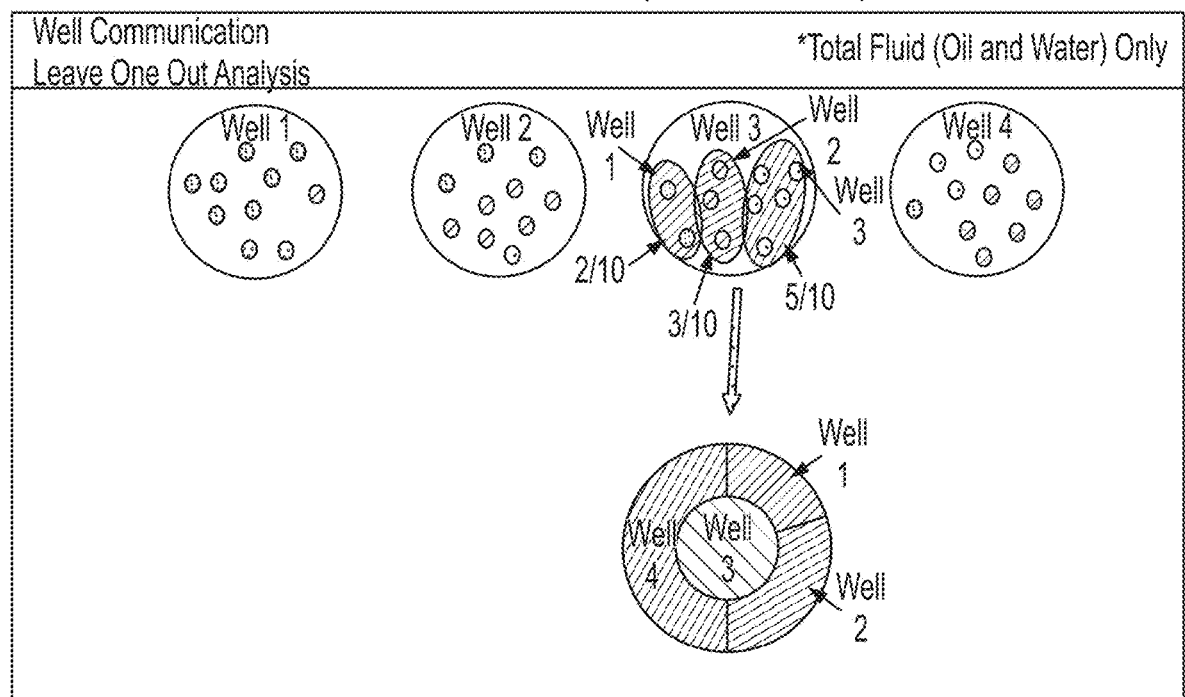
FIG. 7 illustrates how the phenotypic microbial composition analysis allocates microbes as originating from a particular well.

FIG. 7 illustrates how the "leave one out" statistical method used by SourceTracker operates from a simplified perspective looking at one sample per well. Each of four wells has a different microbial composition. Here, the set of wells for analysis includes four—Well 1, Well 2, Well 3, and Well 4. Initially, the microbial composition for Well 3 is left out to determine the most likely source for the microbes present in Well 3. Of the ten microbes, two are initially determined to most likely be sourced from Well 1, three are determined to be sourced from Well 2 and five to most likely be sourced from Well 4. This analysis initially presumes for each well that there are no microbes unique to the well being left out of the analysis. Here, the same analysis would occur for each of the four wells resulting in probabilities for the source of all microbes in any analyzed well.

Figure 8:
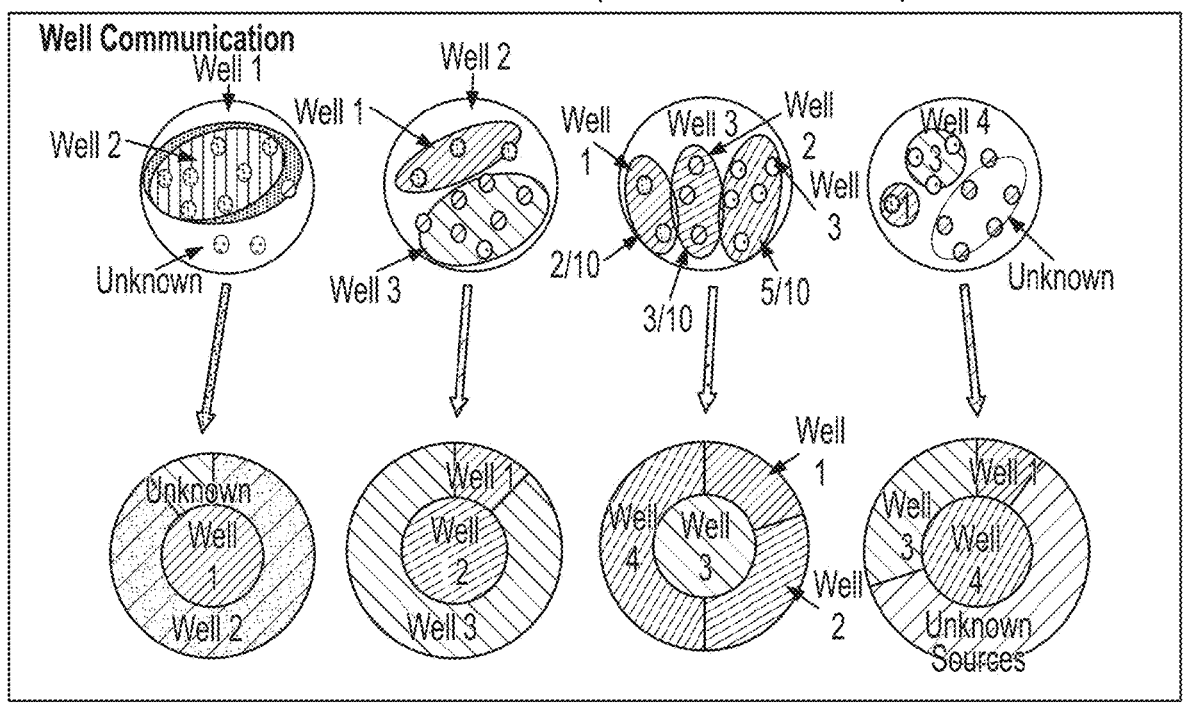
FIG. 8 illustrates how the phenotypic microbial compositions of nearby wells demonstrates communication paths.

FIG. 8 illustrates the results of the full analysis that performs the leave one out method for each of the wells, thus determining the probabilities of the source of all microbes for each well. As shown, Well 1 contains an unknown fraction of microbes and another fraction determined to have a statistically significant probability of being sourced from Well 2, which indicates communication between Well 1 and Well 2. There are statistically significant probabilities that the microbes in Well 2 are sourced from both Well 1 and Well 3, which indicates that Well 2 is in communication (containing a path between in which fluid is flowing) with Well 1 and Well 3. Well 3 has statistically significant probabilities that microbes present are sourced from Wells 1, 2, and 4, thus indicating communication with all three. Well 4 has microbes sourced from Wells 1 and 3 and an unknown fraction. This suggests that Well 4 is in communication with Wells 1 and 3 but not Well 2.

FIG. 9 illustrates how communication between wells may change over time. In this example, the set of wells being analyzed contains ten wells. Each pie chart represents a well in this set, each of which contains a different phenotypic microbial composition. On the left, communication paths are illustrated by the ellipses connecting the individual wells. Here, the well communication analysis represented on the left occurred after a gas lift install. The primary communication between the wells in this example occurs vertically with two groups of wells in communication. The graph on the right in FIG. 9 shows well communication among the set of wells after additional wells (not shown) are put online. As shown, the well communication switched from predominantly vertical to predominantly horizontal.

In one embodiment, an OTU Table may be used as the input to SourceTracker and the resulting probabilities converted from probabilities by OTU to probabilities by phenotype by using PICRUSt software, FABROTAX software, or the rules as set forth in Table 1, including as implemented in computer software. In an alternative embodiment, an OTU Table is converted to a table of phenotypic microbial compositions before being used as an input to SourceTracker or as an input to computer software that performs substantially similar statistical analysis to that performed by Source-Tracker in order to identify probabilities for the sources of microbial phenotypes. In both embodiments, the result is a simplification of the data.

Determining well communication solely using an OTU Table and mapping file as inputs to SourceTracker (or other equivalent software to perform similar statistics, such as Bayesian statistics, to identify the probabilities of potential sources for a given microbe) may provide inaccurate and confusing results. In certain embodiments, the genetic analysis and conversion to an OTU Table is as described herein. However, phenotypic information is used to refine the analysis to more accurately reflect the sources of microbes in the wells of interest and correct for any operational effects or data that may skew the statistical analysis.

One correction that may be performed is to remove the predominant phenotypes of microbes and re-do the analysis. There are at least two ways to accomplish this correction. Where the microbial composition analysis indicates that a microbe (or phenotype) is present at 50% or more in a sample, the OTUs for those microbes may be removed from the OTU Table and then the revised OTU Table used as an input to re-run the statistical analysis for well communication. Alternatively, the output of the statistical analysis for well communication may be filtered to remove the top 1%, top 3%, or top 5% of values.

In certain embodiments, corrections are also made for certain other well treatments and conditions, particularly when well communication is being analyzed at multiple time points. For example, if there is known surface equipment failure, the diversity of the microbial composition tends to go down. If data from the well that has had a surface equipment failure, such as a pump failure, is used in the statistical analysis, the result will not be reflective of well communication. A gas lift install often creates the opposite effect from a surface equipment failure such that the diversity of microbes increases. In both the gas lift install and surface equipment failure scenarios, it may be preferable to exclude the data for the impacted well in the statistical analysis and rely on data from other sampling time points to assess well communication of the impacted well with other wells in the field.

Other situations that require correction include failed tubing requiring repairs or lift revisions. Both those situations provide an opportunity for contaminant introduction. It therefore may be necessary to identify any changes in microbial composition from prior to and after failed tubing repairs or lift revisions and remove the microbes identified as "new" from well communication analysis of those wells. Alternatively, samples from the time point immediately after the failed tubing repairs or lift revisions may be excluded from the well communication analysis.

Certain treatments, for example, acid dumps, paraffin and corrosion treatments, and iron/scale/corrosion treatments, may have an impact on certain phenotypes of microbes and not others. That differential impact can result in the increase or decrease in percentage of certain microbes in subsequent samples from the treated well. That change in microbial composition is not reflective of well communication but rather the impact of the treatment. If phenotypic microbial compositions of the same well(s) at different time points are visually plotted on a graph using color-coding, it may be easy to identify which phenotypes are impacted by such treatments and remove the microbes falling in those phenotypes from the well communication analysis. The same correction may be made without graphing microbial compositions by analyzing statistically significant changes in the microbial compositions of samples before and after the treatment and removing those microbes from the well communication analysis that exhibited a significant change in percentage. For example, if looking at phenotypic microbial compositions before and after an acid dump and the relative abundance of *Halanaerobium* sp. significantly increased (for example, from 10% to 80%), one may correct for the effect of the treatment by removing *Halanaerobium* sp. from the well communication analysis.

To the extent available, the result of well communication analysis may be compared with pressure gauge information. As discussed above, pressure data can be very expensive. Typically, a pressure gauge may be present either at the top of the well, referred to as a top-hole gauge or a surface gauge, or at the bottom of the well, referred to as a bottom-hole gauge. When a surface gauge is used, the actual pressure data is modeled based on the pressures recorded at the surface gauge and algorithms based on physics (e.g., to correct for hydrostatic pressures). In contrast, when a bottom-hole gauge is used, the recorded pressures are the actual pressures. A bottom-hole gauge typically sits at the bottom of the vertical section of the well and continuously provides pressure measurements. When producing from a set of wells and monitoring pressure, typically one well is brought online (into production) at a time. The influence of adding each well to the pressure may be measured as additional wells come online. If a well is shut-in (not producing) the pressure should be constant (a horizontal line if graphed) but a producing well will not produce constant pressures. To the extent a shut-in well shows declining pressure, that indicates fluid is being stolen from another well online that the shut-in well is in communication with. The phenotypic microbial composition analysis may help determine which online well is stealing the fluid from the shut-in well, and the operator may decide to also shut-in the stealing well in order to increase pressure and maximize production from other wells in the area.

Not only is pressure data expensive but sometimes the effects of multiple wells online cannot be distinguished, sometimes the gauges may be lost in the well, and sometimes the batteries for the gauges fail and pressure data is not recorded. Therefore, even if the operator intended to use pressure data to determine well communication (or frac height), there are conditions that render the pressure data either confounding or nonexistent. The phenotypic microbial composition analysis for determining well communication described herein may be used to determine which wells are in communication, whether alone or in combination with pressure data confirming communication. An operator may switch or decide to use phenotypic microbial compositions to determine well communication (or frac height) in the middle of an operation. Thus, rather than shutting down a well to reinstall a pressure gauge, operations may continue while taking samples to use to determine the phenotypic microbial compositions and thus well communication or frac height.

In addition, an operator may choose to monitor well communication (or frac height) using phenotypic microbial compositions in a set of wells, while validating the results with only a select few of the set of wells in order to minimize costs.

Sometimes a well begins to function unusually with no indication on the surface for why that occurred. Phenotypic microbial composition analyses may be used in those situations as a troubleshooting technique to determine what changes have occurred below the surface. For example, these analyses may demonstrate that frac fluids have unexpectedly appeared in the well.

E. Frac Height

As a general matter, frac height shows where the hydrocarbons and/or water are moving from in the vertical direction. Frac height is a measure of the distance of fractures from the wellbore, whether that distance is measured above or below the horizontal wellbore. Frac height may change over time. After fracturing, frac height is expected to be at a maximum. Over time, the fractures may begin to close, particularly in areas where the proppant did not reach, thus limiting the flow of hydrocarbons. Alternatively, additional fracturing activities nearby may cause pressure changes that impact frac height in a given well.

FIG. 10 illustrates an example of how frac height may change over time. Specifically, FIG. 10 shows frac height of four different wells across a five month period (March to August). In this example, Well 1 was down and sampling was not possible in March, May, and June. The vertical line is the average value. The landings for Wells 1, 2, and 4 are each represented by a dotted horizontal line. Each horizontal solid line represents the probability that microbes came from that depth. For each time point with data, a polynomial fit curve is also shown and in this instance represents a five-level polynomial fit to the data. Ideally, the level of polynomial used to fit the data should be set to the number of peaks in the data plus one; however, the additional accuracy above a five level polynomial fit has been shown to be minimal. In most applications contemplated herein, a four or five level polynomial fit is appropriate. As illustrated in FIG. 10, over time, the wells tend to drain from closer to the landing.

Figure 11:
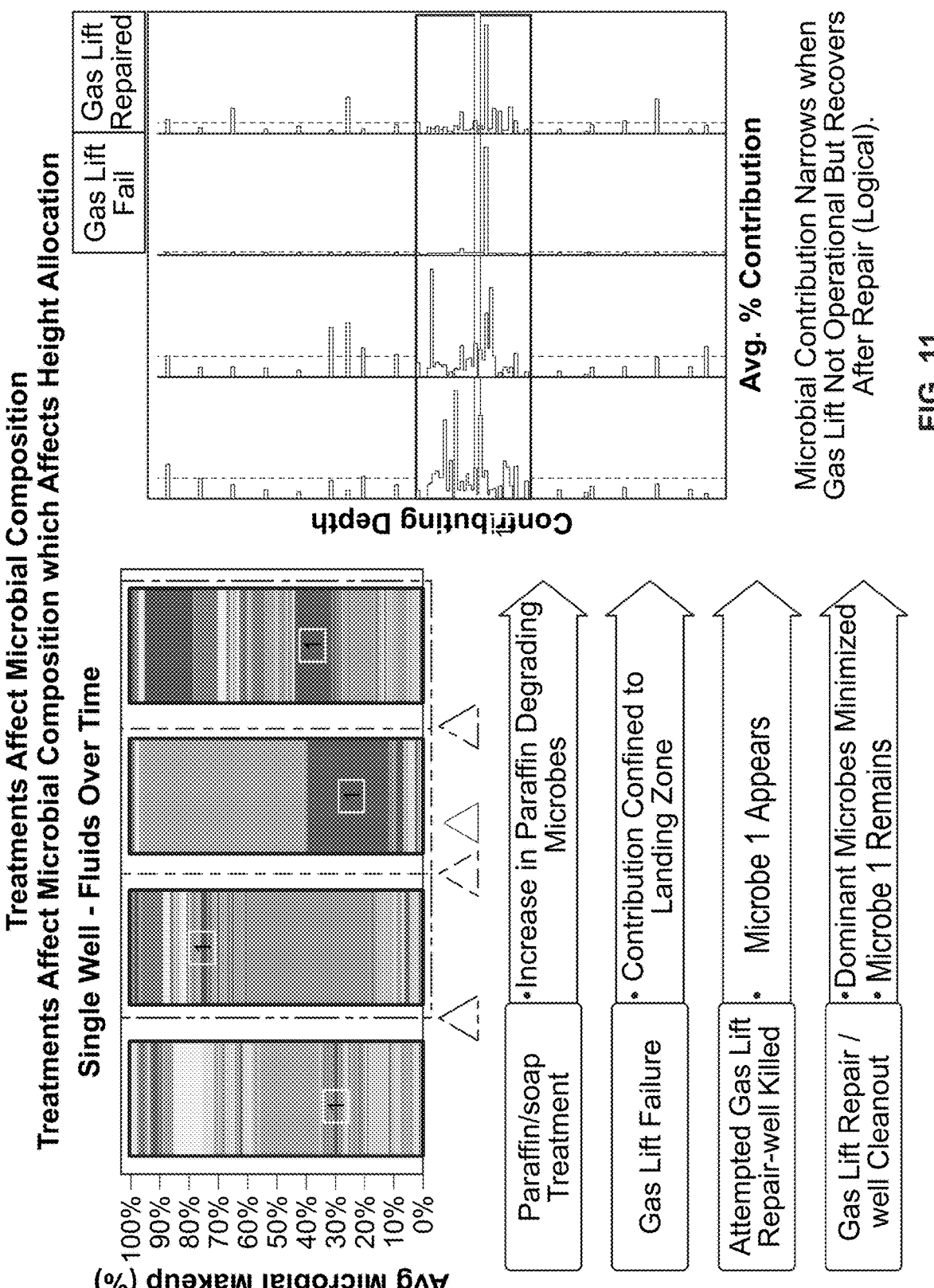
FIG. 11 illustrates how various treatments and operations affect height allocation.

FIG. 11 illustrates how various treatments and drilling operations may affect microbial compositions and thus frac height allocation. The graph on the left represents the phenotypic microbial compositions of a single well over time and in response to various treatments. Specifically, the four treatments/drilling operations are: a paraffin and soap treatment (resulting in an increase in paraffin degrading microbes), a gas lift failure, an attempted gas lift repair where the well was killed (*Halanaerobium* sp. appeared), and a gas lift repair with well cleanout (dominant microbes minimized, *Halanaerobium* sp. remain). As shown, each of these treatments or operations resulted in a substantial change to the phenotypic microbial composition of the well. As shown on the right in FIG. 11, the microbial contribution to frac height allocation narrows when the gas lift is not operational but recovers after repair. To minimize the impact of these treatments and drilling operations on the frac height calculation, microbes may be removed from the frac height analysis as described above for the well communication analysis.

In order to determine frac height using the methods described herein, it is useful to take samples as described above and identify whether each sample is a "source" or "sink." In this context, a "source" refers to a sample that may introduce microbes into the system, and a sample that may include microbes from the natural environment or originating from a source is referred to as a "sink." Due to the very nature of microbial movement and fracturing conditions, the microbial population of a sink may reflect microbes originating from the natural environment (e.g., microbes found in the geological formation where fracturing is occurring) and microbes introduced by the process (e.g., microbes added by virtue of injected drilling mud or other drilling fluids).

As described above for well communication, Source-Tracker software (or similar algorithms or software implementing similar statistics, such as Bayesian statistics) may be used to determine where the microbes are coming from in produced fluid, thus providing an indication of frac height because the depths of solid samples used for reference are known. The user performs microbial composition analysis as described above and uses the resulting data for each sample as the input, along with an indication of whether the sample represents a source or a sink, to SourceTracker. For this purpose, rock (cuttings or core samples) is identified as a source, produced fluid is identified as a sink, and injected fluid or mud is identified as a source. SourceTracker performs a statistical analysis to determine the probability that the microbial composition of a sample (if that is what is used as the input) came from a particular source. In the use of SourceTracker for determining frac height, the goal is to determine from what rock-specifically representing a zone or area in the formation at a known depth—the microbes in the sample of produced fluid came from. The distance from that known depth to the wellbore is the calculated frac height for that sample. In certain circumstances, the calculated frac height over multiple samples may be averaged to determine an average frac height for a particular well or stage of a well. If analyzing individual stages of a well, cuttings from the horizontal zone near the stage may be used.

If the produced sample contains both oil and water, it is important to understand the impact that water may have on the calculated frac height. The microbial compositions of a fluid sample (including phenotypic microbial compositions) from produced fluids looks at total fluids (i.e., hydrocarbons and water). Traditional geochemical techniques, such as those described in U.S. Pat. Nos. 10,585,078 and 10,760,418, typically only focus on the hydrocarbon portions. In one embodiment, both microbial composition analysis and geochemical techniques are performed from well samples and combined with petrophysical outputs in order to determine which zones are contributing the majority of which fluid type. Petrophysical outputs, such as electrical logs, mud logs, and drilling reports, provide a description of the rock materials, estimates of fluid within the pore space, and the proportions of fluids before the well is hydraulically fractured and produced. In this embodiment, an initial microbial composition analysis is performed on cuttings samples taken at various depths, either from the well as it is being drilled or from a nearby pilot well. The initial microbial composition analysis (microbial compositions of the cuttings samples at known depths) is then compared to the microbial composition analysis of fluid samples as the well is fractured and/or produced. Specifically, samples are taken and analyzed as described herein to determine frac height and any changes in frac height over time. At the same time, geochemistry is used to determine a hydrocarbon height. By comparing the frac height of total fluids (as derived from phenotypic microbial composition analysis) with the height of the hydrocarbons, such as by plotting the two on a graph, areas or zones with a majority water can be identified and how zone contributions change over time may be determined. When the above analysis identifies zones or areas of large contributions from water, the operator may choose not to drill a new well in that same zone or area or not to frac stages of a well in that zone or area in order to minimize the amount of water being produced and maximize the production of hydrocarbons.

Figure 12:
FIG. 12 illustrates petrophysical data, geochemical data, and frac height data determined by microbial composition analysis for one well.

FIG. 12 illustrates static petrophysical data (columns 1-5) with dynamic height allocation from geochemical data (column 6) and from microbial analysis (OxyDNA) (columns 7-9) for one well. Each of A-F represents an individual depth, with those depths equally spaced. The first column "Gamma Ray" presents gamma ray data at the depths shown. The second column identifies the depths. The third column shows neutron, density, photoelectric factor (PEF) and sonic data at the depths shown. The fourth column shows lithologic mineralogy data, and the fifth column shows bulk volume fluids data. These first five columns represent data generally classified as petrophysical data and represent the initial conditions present at the time of drilling. The sixth column contains geochemical data along the depths of interest. The seventh through ninth columns contain frac height data along the depths of interest. Column 7 uses frac height data as determined from the microbial composition analysis. Column 8 restricts the frac height data from column 7 to only those depths that demonstrate greater than a 20% contribution through time per depth. At every depth, if the cumulative number of dates that have a fluid contribution greater than 3% is at least 20% or greater, then it is given a 1 and counted. The resulting curve, as illustrated in Column 8, highlights the main contributing benches to hydrocarbon production. Column 9 overlays the Column 7 and Column 8 data. The depths (or benches) where there is overlap between the geochemical data and the microbial analysis data indicate those that are predominantly contributing hydrocarbons. The depths (or benches) where there is no overlap between the geochemical data and the microbial analysis data indicate those that are predominantly contributing water. Those results may be compared to the petrophysical data to determine if they make sense. If there is a bench where the methods show it should be hydrocarbon bearing and the bulk volume fluids data shows a much higher proportion of oil than water, this makes sense physically. Additionally, lithology and geomechanical properties of the formation can be used as a physical cross check to where the methods are indicating the fracture growth has reached.

Frac height gives an indication of where the wells are draining from and that may be correlated with data regarding production from those wells in order to determine where new wells should be drilled. For example, if a particular frac height demonstrates a high level of oil production in one well at a particular depth, another well located nearby may be drilled to that depth to tap more directly into the reservoir. In addition, how frac height changes over time and the impact that has on production may be used to determine where to drill new wells and/or what stages to frac. For example, if a particular zone has a drastic decrease in frac height over time for one well, an operator may decide not to frac that zone in nearby wells. The operator may also decide not to frac at the same depth in new wells close to a well that is producing a large proportion of hydrocarbons so that the new wells are not draining from the same place as the other well. More specifically, if frac height analysis demonstrates that two wells with a vertical distance of greater than 100 feet had nearly the same overlapping drainage heights, then only one well may be needed to drain the area. In that situation, an operator may choose to drop the upper landing zone in a third well being drilled rather than continue to drill wells to drain from the same zone as where the first and second wells are draining from.

As another example, frac height may be used by an operator to determine how many new wells to drill in a field or area of a field. The frac height analysis of multiple wells may indicate large reserves of hydrocarbons at multiple depths, and the operator may decide to drill new wells at each of those depths in order to maximize production.

Based on well communication and/or frac height data derived from phenotypic microbial compositions, the operator may decide what strategy to use to maximize production, for example, shutting in a well in communication with another shut-in well in order to increase pressure (and therefore production) from other online wells in the field. As another example, an operator may desire to optimize contribution from a set of wells in communication. The operator will seek to optimize the surface area from which drainage is occurring so that the set of wells is draining in a way in which the drainage boundaries touch but do not negatively interfere with the drainage of each. If the operator notices a drainage issue and well communication analysis determines that one well is stealing hydrocarbons from another well, the operator may decide to shut in one of those wells because the operation of both is not efficient.

In addition, frac height and well communication may be used by the operator to determine the geometry of additional wells. For example, the operator may use an analysis of well communication information to determine that there is more drainage occurring from the flow of hydrocarbons between wells in a specific direction and drill and fracture a new well such that its flow is in the same direction.

Additional processing of the data may be used to generate more accurate frac height calculations. For example, data from contaminant microbes could be removed from the data set prior to determination of frac height. Contaminant microbes may be those identified as present in samples of the injected fluid or drilling mud or those only identified after drilling because those microbes are not likely informative as to source.

Further, it is impossible that all fluids sampled would come from a single depth after fracturing has occurred. If the data set indicates that all of the fluids appear to come from a single depth, there likely are one or more outliers skewing the results. Those outliers can be removed from the data set, and in some cases that involves removing the top 1% of the values (i.e., the value predicted to come from that depth), allocated by SourceTracker (or other similar algorithms or software) the top 3% of values, or the top 5% of values.

Another correction is to remove from the OTU Table OTUs for microbes not present in rock samples and re-rerun the statistical analysis. By removing microbes only in fluid samples, the potentially contaminant effects of fluids injected into the well can be minimized. One may also correct for potential contamination coming from mud used in drilling or well treatments by removing any microbes identified in samples of the mud from the statistical analysis. Ideally, the microbes to be removed in a mud correction step are identified by microbial composition analysis of mud samples from when the well is drilled and samples from each time the constituency of the mud changes, such as for instance, there is a change in the salinity, fluid type (i.e. water-based mud to oil-based mud) and/or additives like barite are added.

In addition, sampling of the rock (through cuttings or core samples) may occur more frequently at certain depth ranges and skew the statistical analysis. To correct for this, one may only use data from equally spaced samples of the rock for the statistical analysis. For example, if rock samples exist for depths of 1000, 1010, 1020, 1030, 1050, 1060, 1090, and 1120 feet, one may remove the data for samples at 1010, 1020, and 1050 so that the spacing between depths at which the rock was sampled is consistently 30 feet for the samples used in the analysis.

EXAMPLES

The following are prophetic examples.

Example 1: Phenotypic Microbial Composition Analysis

A set of four wells in the Marcellus Shale will be analyzed for phenotypic microbial compositions. The geometry of the wells at the surface (i.e., the locations of the wellheads) will be as follows. A pilot well will be located in the center with the four wells of interest located 1200 feet from the pilot well in the North (Well 1), East (Well 2), South (Well 3), and West (Well 4) directions. This square or diamond arrangement of wells around the pilot well will result in a distance of approximately 1697 feet between Well 1 and Well 2, Well 2 and Well 3, Well 3 and Well 4, and Well 4 and Well 1 on the surface. This arrangement will result in a distance of 2400 feet on the surface between Well 1 and Well 3 and between Well 2 and Well 4.

Cuttings samples are taken every 30 feet from the pilot well. For each of the four wells of interest, fluid samples are taken from the wellhead and therefore are anticipated to be comprised of both hydrocarbons and water (Samples 1 to 4). An additional two samples, Samples 5 and 6, were taken from injected fluids. For each fluid sample, an operator will take 50 ml of produced fluid from the wellhead and put into a conical polypropylene/high density polyethylene centrifuge tube that is non-pyrogenic, non-cytotoxic, DNase/RNase-free and human DNA free. Each sample will be kept in a freezer to be shipped from the field to a nucleic acid sequencing facility. For each cuttings sample, the operator will separate the cuttings from drilling mud using a shale shaker and place each cuttings sample into a sterile sample bag marked with the depth that the cuttings came from and then place each sample in a freezer until shipping to a nucleic acid sequencing facility.

The samples will then be shipped to a nucleic acid sequencing facility. At the sequencing facility, each cuttings sample is milled using a grinder with a stainless steel blade to pulverize the rock. Between each cuttings sample, the grinder will be wiped down with 70% ethanol to prevent any cross-contamination. Only 0.25 grams of each cuttings sample will be used for further analysis. The standard protocol of the MoBio PowerSoil DNA Extraction kit (Qiagen, USA) is then used to extract nucleic acids from the samples. Fluid samples will each be thawed and then filtered using a 0.22 μm filter. Extraction of nucleic acids will then be performed by using the standard protocol of the MoBio PowerSoil DNA Extraction kit.

The extracted nucleic acids of each sample will then be sequenced by next generation sequencing. The following primers will be used to amplify the V4 variable region of 16S rDNA of each sample: Primer 515 (GTGY-CAGCMGCCGCGGTAA) and Primer 806 (GGAC-TACNVGGGTWTCTAAT). A barcode will be used on the forward primer in order to allow identification of each sample. Amplification will be performed using PCR with the HotStarTaq Plus Master Mix Kit (Qiagen, USA) under the following conditions: 94° C. for 3 minutes; 28 cycles of 94° C. for 30 seconds, 53° C. for 40 seconds, 72° C. for 1 minute; and a final elongation step at 72° C. for 5 minutes. Following amplification, samples will be pooled and purified using AMPure XP beads (AMPure XP for PCR Purification Kit, Beckman Coulter, USA). The purified PCR products will then be used to prepare a nucleic acid library with adapters by following the Illumina TruSeq DNA library preparation protocol (Illumina, San Diego, California). The library will then be loaded onto a flow cell where fragments are captured on a lawn of surface-bound oligonucleotides complementary to the library adapters. Each fragment is then amplified into distinct, clonal clusters. Sequencing is then performed on an Illumina MiSeq (Illumina, USA). The resulting FASTQ data file will then be demultiplexed by assigning each cluster to a specific sample based on the barcode added during library formation so that the data is then a set of raw sequences by sample.

These raw sequences will then be input to CLC Workbench (Qiagen, USA) to align the raw sequences with sample sequences of known microbial sequences with a 97% homology setting for the alignment. CLC Workbench will then provide an OTU Table. The OTU Table (with Greengenes identifiers) will then be converted to microbial phenotypes using PICRUSt and/or FAPROTAX software to provide an abundance in each sample by phenotype. In this way, the original OTU Table will be converted into a table comprised of phenotypic microbial compositions per sample. The abundances of any microbes whose OTU is not converted into a phenotype will be combined as the unclassified fraction for each sample.

After the analysis described above, the phenotypic microbial compositions will be identified as shown for example in Table 2.

TABLE 2

| Phenotypic Microbial Compositions by Percentage | | | | | | |
|---|---|---|---|---|---|---|
| Phenotype | Sample 1 | Sample 2 | Sample 3 | Sample 4 | Sample 5 | Sample 6 |
| Acid Producing | 88.59% | 15.72% | 1.29% | 13.04% | 29.27% | 3.36% |
| H2S Producing | 2.66% | 31.48% | 59.65% | 56.87% | 43.08% | 52.36% |
| H2S Producing/Acid Producing | 0.06% | 1.31% | 33.77% | 0.16% | 1.27% | 3.06% |
| Methane producing | 0.24% | 2.85% | 0% | 0.10% | 0.16% | 0.48% |
| Microbial Induced Corrosion/ Iron Reducing Bacteria/H2S Producing | 0.05% | 0.21% | 0.00% | 0.09% | 0% | 0% |
| Microbial Induced Corrosion/ Iron Reducing Bacteria/Nitrate Reducing Bacteria | 8.4% | 48.43% | 5.29% | 29.74% | 26.22% | 40.74% |
| Radiation Resistant | 0% | 0% | 0% | 0% | 0% | 0% |

Example 2: Well Communication Analysis

In one way to determine well communication, samples will be taken, nucleic acids sequenced, and an OTU Table generated as described above for Wells 1 to 4 in Example 1. The OTU Table will be converted to a Phenotypic Table by either using PICRUSt software or applying the rules of Table 1. With that conversion, the composition percentage of OTUs that fall into the same phenotype will be combined such that the Phenotypic Table contains composition percentages by phenotypes. For each phenotype, one of the Greengenes identifiers for a microbe within the phenotype will be maintained in the table or a unique numerical identifier will be used for each phenotype. SourceTracker software will then be used to identify the source of microbial phenotypes for each of the four wells of interest. The cuttings samples will be each identified as formation and a source in this analysis, and the fluid samples are each identified as sinks. Because the cuttings samples are identified as sources in this analysis, any confounding influence of the microbes present in the formation will be controlled for and minimized in the analysis. The output of the SourceTracker analysis will provide probabilities for the source of microbial phenotypes found in each of the four wells and thus identify which wells are in communication. For example, if two phenotypes of microbes are found in Well 2 that have a high probability (as used herein "high probability" means a probability above the average of probabilities for the potential sources) of being sourced from Well 1, then it is likely that communication pathways exist between Well 1 and Well 2. Conversely, if Well 4 shows a unique phenotypic microbial composition for which the data indicates very low probabilities (as used herein "low probability" means a probability lower than the average of probabilities for the potential sources) of being sourced from any of the other wells, it is likely that no communication pathways exist between Well 4 and any of the other wells.

Example 3: Well Communication Analysis

In another way to determine well communication, samples will be taken, nucleic acids sequenced, and an OTU Table generated as described above for Wells 1 to 4 in Example 1. The OTU Table with Greengenes identifiers and a mapping file that includes the name of each sample and whether that sample is considered a source or sink will be input to SourceTracker software for an analysis of the source of microbes for each of the four wells of interest. The cuttings samples will be each identified as formation and a source in this analysis, and the fluid samples are each identified as sinks. Because the cuttings samples are identified as sources in this analysis, any confounding influence of the microbes present in the formation will be controlled for and minimized in the analysis.

The output of the SourceTracker analysis will provide probabilities for the source of microbes found in each of the four wells. The probabilities will then be transformed into more usable data by converting the individual microbes into phenotypes and analyzing the probabilities by phenotype. For example, five identified OTUs present in a sample may be combined into a single phenotype, for example all five OTUs may have the phenotype of hydrocarbon degraders. By combining the probabilities of those five OTUs into a single probability regarding hydrocarbon degraders, the data is simplified and it is easier to draw conclusions about well communication.

For example, if two phenotypes of microbes are found in Well 2 that have a high probability (above the average of probabilities for the potential sources) of being sourced from Well 1, then it is likely that communication pathways exist between well 1 and Well 2. Conversely, if Well 4 shows a unique phenotypic microbial composition for which the data indicates very low probabilities (lower than the average of probabilities for the potential sources) of being sourced from any of the other wells, it is likely that no communication pathways exist between Well 4 and any of the other wells.

Given the lack of communication between Well 4 and the other wells currently in the field, an operator may choose to drill Well 5 and fracture that well to open up communication paths with Well 4 in order to optimize production. To do so, the operator would control pressure in the field, including by shutting in other wells as necessary, such that the fractures of Well 5 will occur in the direction of Well 4.

Example 4: Using Phenotypic Microbial Composition Analysis to Determine Frac Height Cuttings samples and both produced and injected fluid samples will be used to determine frac height of Well 1. An operator will collect cuttings and produced fluid samples as described above for Example 1. The operator will also collect 50 ml injected fluid samples in the same type of centrifuge tubes as described above for produced fluid samples but the operator will take those samples from the fluid being injected into the wellhead before injection. For all of the samples, nucleic acids will be extracted and sequenced, and the microbial compositions determined as set forth in Example 1, with that process the same for both produced and injected fluids except as to the identification of a sample as a source or sink for the mapping file to be used in SourceTracker. For a frac height analysis of Well 1, cuttings samples will be identified as a source, produced fluid will be identified as a sink, and injected fluid samples will be identified as a source. In this way, any confounding influence of microbes introduced by the injection of fluid into the well may be minimized. In the case of frac height analysis, cuttings samples may be named by depth in order to provide an indication of the source of microbes into the production fluid. The output of SourceTracker will therefore provide probabilities as to the source of microbes (or phenotypes of microbes) in produced fluid, which will either indicate the microbes (or phenotypes of microbes) came from the injected fluid (and therefore may be disregarded) or came from a particular depth in the formation.

Frac height will then be calculated by finding the difference between the depth at which the microbes present in the produced fluid most likely came from with respect to the known landing (i.e., the depth of where the horizontal wellbore is in the formation). To do this calculation, a five level polynomial fit is made to the probabilities that the microbes in the produced fluid samples came from a particular depth, and the maximum of that fit is used for the frac height calculation. The range of the distribution around a single curve represents the most realistic frac height. FIG. 13 illustrates polynomial fits to frac height data to calculate the frac height (the distance from the deflection point in the polynomial curve to the landing).

An operator may find it advantageous to drill a new well directly into the formation at a frac height, which has shown high contribution for Well 1. In this example, the frac height, as calculated above, will be used as the targeted landing zone for the new well and the new well will be located within 1500 feet of Well 1.

REFERENCES

Atlas, Ronald M. and Bartha, Richard. Microbial Ecology: Fundamentals and Applications, 2$^{nd}$ ed. Menlo Park, CA: Benjamin/Cummins Publishing Co., 1987.

Bastin, E. S. "The Presence of Sulfate Reducing Bacteria in Oil Field Waters." Science (1926) 63:21-24.

Bastin, E. S., et al. "The Problem of the Natural Reduction of Sulfates." Bull. Am. Proc. Petrol. Geol. (1926) 10:1270-1299.

Colwell, R. R. "Genetic and Phenetic Classification of Bacteria." Advances in Applied Microbiology (1973) 16:137-176.

DOE/NETL-2014/1671. Summary of Costs Associated with Seismic Data Acquisition and Processing. Apr. 12, 2013 (Rev 3)

Dreyfus, Sebastian L., et al. U.S. Pat. No. 10,330,659. "Method for Determining the Location, Size, and Fluid Composition of a Subsurface Hydrocarbon Accumulation." Issued Jun. 25, 2019.

Economides, Michael J. and Martin, Tony. *Modern Fracturing: Enhancing Natural Gas Production*. Houston, TX: BJ Services Co., 2007.

Economides, Michael J. and Valko, Peter. *Hydraulic Fracture Mechanics*. New York: John Wiley & Sons, 1995.

Economides, Michael J. and Wang, Xiuli. "Chapter 2 Natural Gas Production" In: Economides, Michael J. and Martin, Tony. *Modern Fracturing: Enhancing Natural Gas Production*. Houston, TX: BJ Services Co., 2007.

Gyllenberg, H. G. "Character Correlations in Certain Taxonomic and Ecologic Groups of Bacteria: A Study Based on Factor Analysis. Annals of Society of Experimental Biology in Finland (1965) 43:82-90.

Holder-Franklin, M. A., M. Franklin, P. Cushion, C. Cormier, and L. Wuest. "Population Shifts in Heterotrophic Bacteria in a Tributary of the Saint John River as Measured by Taxometrics." In M.W. Loutit and J.A.R. Miles (eds.) *Microbial Ecology*, Springer-Verlag, Berlin, pp. 44-50.

Howard, G. C. and C. R. Fast. *Hydraulic Fracturing*. New York: Society of Petroleum Engineers of AIME, 1970.

Hubbert, M. K. and Willis, D. G. "Mechanics of Hydraulic Fracturing, Trans. AIME, 210, 153-166, 1957.

Knight, Rob, et al. "Microbiome Based Systems, Apparatus and Methods for the Exploration and Production of Hydrocarbons." U.S. Pat. No. 9,771,795. Issued Sep. 26, 2017.

Knight, Rob, et al. "Microbiome Based Systems, Apparatus and Methods for the Exploration and Production of Hydrocarbons." U.S. Pat. No. 10,767,476. Issued Sep. 8, 2020.

Knight, Rob, et al. "Microbiome Based Systems, Apparatus and Methods for the Exploration and Production of Hydrocarbons." U.S. Pat. No. 10,975,691. Issued Apr. 13, 2021.

Knight, Rob, et al. "Microbiome Based Systems, Apparatus and Methods for the Exploration and Production of Hydrocarbons." U.S. Pat. No. 11,028,449. Issued Jun. 8, 2021.

Knight, Rob, et al. "Microbiome Based Systems, Apparatus and Methods for the Exploration and Production of Hydrocarbons." U.S. Pat. No. 11,047,232. Issued Jun. 29, 2021.

Knight, Rob, et al. "Microbiome Based Systems, Apparatus and Methods for the Exploration and Production of Hydrocarbons." U.S. patent application No. 20210010370. Published Jun. 14, 2021.

Langille, M. G. I., Zanevald, J., Caporaso, J. G., McDonald, D., Knights, D., a Reyes J., Clemente, J. C., Burkepile, D. E., Vega Thurber, R. L., Knight, R., Beiko, R. G., and Huttenhower, C. "Predictive functional profiling of microbial communities using 16S rRNA marker gene sequences. Nature Biotechnology, 31 (9), 814-823. Published Aug. 25, 2013.

Liu, Yifei and Wu, Jiang. U.S. Pat. No. 10,585,078, "Three-Dimensional Unconventional Reservoir Monitoring Using High-Resolution Geochemical Fingerprinting." Assigned to Revochem LLC, issued Mar. 10, 2020.

Liu, Yifei and Wu, Jiang. U.S. Pat. No. 10,760,418. "Method and System for Preserving and Obtaining Hydrocarbon Information from Organic-Rich Rock Samples." Assigned to Revochem LLC, issued Sep. 1, 2020.

Michael, Gerald Eric and Jokanola, Olufemi Akande. U.S. Pat. No. 8,666,667. "Hydrocarbon Production Allocation Methods and Systems." Assigned to ConocoPhillips Co., issued Mar. 4, 2014.

Nolte, Kenneth G. "Determination of Fracture Parameters From Fracturing Pressure Decline." SPE 8341 September 1979.

Nolte, Kenneth G. and Smith, Michael B. "Interpretation of Fracturing Pressures." Society of Petroleum Engineers, September 1981.

Robinson, J. A. "Determining Microbial Kinetic Parameters Using Nonlinear Regression Analysis." Advances in Microbial Ecology (1985) 8:61-114.

Rosswall, T. and E. Kvillner. "Principle-Component and Factor Analysis for the Description of Microbial Populations."

Sneath, P. H. A. and R. R. Sokal. *Numerical Taxonomy: The Principles and Practice of Numerical Classification*. W.H. Freeman and Company, San Francisco, 1973.

Sokal, R. R. and F. J. Rohlf. *Biometry*. W.H. Freeman and Company, San Francisco, 1981.

Steel, R. G. D. and J. H. Torrie. *Principles and Procedures of Statistics: A Biometrical Approach*. McGraw-Hill Book Co., New York, 1980.

Sundman, V. and H. G. Gyllenberg. "Application of Factor Analysis in Microbiology. I. General Aspects on the Use of Factor Analysis in Microbiology." Annals of the Academy of Sciences of Finland Series A IV 112:1-32 (1967).

Sundman, V. "Four Bacterial Soil Populations Characterized and Compared by a Factor Analytical Method." Canadian Journal of Microbiology (1970) 16:455-464.

Sundman, V., "Description and Comparison of Microbial Populations on Ecological Studies with the Aid of Factor Analysis." Bulletin of Ecological Resources Commission (Stockholm) 17:135-141 (1973).

Tucker, Yael Tarlovsky. "Microbiology in Shale: Alternatives for Enhanced Gas Recovery" (2015). *Graduate Theses, Dissertations, and Problem Reports*. 6834 (available at: https://researchrepository.wvu.edu/etd/6834).

Valkó, Peter, and Michael J. Economides. *Hydraulic Fracture Mechanics*. New York: John Wiley & Sons, 1995.

Williams, Bert B., John L. Gidley, and Robert S. Schechter. *Acidizing Fundamentals*. New York: Society of Petroleum Engineers of AIME, 1979.

All of the systems and methods disclosed and claimed herein can be made without undue experimentation in light of the present disclosure. While the compositions and methods of this invention have been described in terms of particular embodiments, it will be apparent to those of skill in the art that variations may be applied to the systems and methods described herein without departing from the concept, spirit, and scope of the invention. Any such variations apparent to those skilled in the art are deemed to be within the spirit, scope and concept of the invention as described and defined by the appended claims.

What is claimed is:

1. A method for well management by assessing well communication comprising:

a. taking at least one sample of produced fluid from each of a first well and a second well at a first time, wherein the first time for taking the produced fluid sample from the first well and the first time for taking the produced fluid sample from the second well may be different;

b. using sequencing information from 16S rDNA to identify a microbial composition of the at least one sample from the first well and a microbial composition of the at least one sample from the second well;

c. removing from each phenotypic microbial composition any microbial phenotype that comprises more than fifty percent of the composition of the sample and recalculating each phenotypic microbial composition prior to step (d);

d. using the microbial compositions to identify at least one microbe or microbial phenotype of the first well that has a high probability of having been sourced from the second well; and e. using the information in step (d) to take an action with respect to a set of wells that includes the first and second well, wherein the action is at least one of the following: (i) shutting in at least one of the first well and the second well before fracturing a third well; (ii) fracturing multiple wells at the same time wherein the multiple wells are in the same formation bench as the first well or the second well; or (iii) drilling a third well to the same formation bench as the first well or the second well.

2. The method of claim 1, wherein each microbial composition is a phenotypic microbial composition.

3. The method of claim 1, further comprising:

i. taking at least one additional sample of produced fluid from each of a first well and a second well at a second time;

ii. using sequencing information from 16S rDNA to identify a microbial composition of the at least one sample from the first well taken at the second time and a microbial composition of the at least one sample from the second well at the second time;

iii. comparing the microbial composition of the sample of the first well at the first time to the microbial composition of the sample of the first well taken at the second time to identify statistically significant changes in the microbial compositions of the first well;

iv. recalculating the microbial composition of the sample of the first well taken at the second time after removing any microbe whose percentage of composition is statistically significantly different between the sample of the first well at the first time and the sample of the first well taken at the second time;

v. comparing the microbial composition of the sample of the second well at the first time to the microbial composition of the sample of the second well taken at the second time to identify statistically significant changes in the microbial compositions of the second well; and vi. recalculating the microbial composition of the sample of the second well taken at the second time after removing any microbe whose percentage of composition is statistically significantly different between the sample of the second well at the first time and the sample taken from the second well at the second time;

vii. wherein step (c) includes using the recalculated microbial composition of the first well from step (iv) and the recalculated microbial composition of the second well from step (vi) to identify at least one microbe or microbial phenotype of the first well that has a high probability of having been sourced from the second well.

4. The method of claim 3, wherein each microbial composition is a phenotypic microbial composition.

5. A method for well management by assessing frac height comprising:

a. taking at least one sample of produced fluid from a first well;

b. taking at least one sample of cuttings from either the first well or a pilot well located more than 10 feet but less than 79,200 feet from the first well;

c. using sequencing information from 16S rDNA to identify a microbial composition for each of the at least one produced fluid sample from the first well and a microbial composition of the at least one cuttings sample;

d. using the microbial compositions of the sample of produced fluid from the first well and the sample of cuttings from either the first well or the pilot well to determine at least one frac height; and e. using the information in step (d) to take an action to increase hydrocarbon production with respect to a set of wells that includes the first well.

6. The method of claim 5, wherein each microbial composition is a phenotypic microbial composition.

7. The method of claim 5, wherein the action is drilling a second well to a landing zone that includes the depth of the frac height determined in step (d).

8. The method of claim 5, wherein the at least one cuttings sample is taken from a pilot well.

9. The method of claim 8, wherein the pilot well is located more than 1000 feet and less than 1500 feet from the first well.

10. The method of claim 5, further comprising:

i. taking at least one sample of oil from the first well; and ii. using sequencing information from 16S rDNA to identify a microbial composition of the at least one oil sample.

11. A method for well management comprising:

a. taking at least one sample of produced fluid from a first well;

b. taking at least one sample of produced fluid from a second well;

c. taking at least one sample of cuttings from either the first well or a pilot well located more than 10 feet but less than 79,200 feet from the first well;

d. using sequencing information from 16S rDNA to identify a microbial composition of the produced fluid sample of the first well, a microbial composition of the produced fluid sample of the second well, and a microbial composition of the cuttings sample;

e. using the microbial composition of the produced fluid sample of the first well and the microbial composition of the produced fluid sample of the second well to identify at least one microbe or microbial phenotype from produced fluids of the first well that has a high probability of having been sourced from the second well;

f. using the microbial composition of the produced fluid sample of the first well and the microbial composition of the cuttings sample to determine a frac height of the first well; and g. drilling a third well to a landing zone that includes the depth of the frac height of the first well determined in step (f).

12. The method of claim 11 wherein each microbial composition is a phenotypic microbial composition.

13. A method for well management by assessing well communication over time comprising:

a. taking at least one sample of produced fluid from each of a first well and a second well at a first time;

b. taking at least one sample of produced fluid from each of a first well and a second well at a second time;

c. using sequencing information from 16S rDNA to identify a microbial composition of each produced fluid sample;

d. using the microbial compositions of the samples taken at the first time to determine whether there is at least one microbe or microbial phenotype of the first well that has a high probability of having been sourced from the second well as of the first time;

e. using the microbial compositions of the samples taken at the second time to determine whether there is at least one microbe or microbial phenotype of the first well that has a high probability of being sourced from the second well as of the second time;

f. comparing the results of steps (d) and (e) to determine whether well communication has changed over time; and g. using the information in step (f) to take an action with respect to a set of wells that includes the first well and the second well, wherein the action is shutting in at least one of the first well or the second well and further includes fracturing a third well in the set of wells.

14. The method of claim 13, wherein each microbial composition is a phenotypic microbial composition.

15. A method for well management comprising:

a. taking a solid sample from a first depth of a first well in a formation;

b. taking a solid sample from at least one second depth of the first well;

c. using sequencing information from 16S rDNA to identify a microbial composition of each solid sample;

d. fracturing the first well;

e. taking at least one produced fluid sample from the first well at each of the first depth and the second depth on at least two different dates;

f. using sequencing information from 16S rDNA to identify a microbial composition of each produced fluid sample;

g. using the microbial compositions of the solid sample and produced fluid sample at each depth and date to determine a frac height;

h. identifying at least one depth where the frac height indicates a fluid contribution greater than 3% on 20% or more of the dates sampled;

i. determining a hydrocarbon height at the depth identified in (h) using one or more of the following analyses: geochemical, gamma ray, neutron, density, photoelectric factor (PEF), sonic, or lithologic mineralogy;

j. comparing the hydrocarbon height at the identified depth to the frac heights at the identified depth to determine whether the produced fluids at the identified depth are primarily contributing hydrocarbons; and k. if produced fluids at the identified depth are primarily contributing hydrocarbons, taking one or more of the following actions: (i) drilling a well in the same formation to the identified depth; (ii) fracturing at least one well drilled to the identified depth in the formation; or (iii) shutting in a well that is not drilled to the identified depth.

16. The method of claim 15, wherein the microbial composition of each produced fluid sample is a phenotypic microbial composition.

17. The method of claim 15, wherein the microbial composition of each cuttings sample is a phenotypic microbial composition.

18. A method for well management comprising:

a. taking a solid sample from a first depth of a first well in a formation;

b. taking a solid sample from at least one second depth of the first well;

c. using sequencing information from 16S rDNA to identify a microbial composition of each solid sample;

d. fracturing the first well;

e. taking at least one produced fluid sample from the first well at each of the first depth and the second depth on at least two different dates;

f. using sequencing information from 16S rDNA to identify a microbial composition of each produced fluid sample;

g. using the microbial compositions of the solid sample and produced fluid sample at each depth and date to determine a frac height;

h. identifying at least one depth where the frac height indicates a fluid contribution greater than 3% on 20% or more of the dates sampled;

i. determining a hydrocarbon height at the depth identified in (h) using one or more of the following analyses: geochemical, gamma ray, neutron, density, photoelectric factor (PEF), sonic, or lithologic mineralogy;

j. comparing the hydrocarbon height at the identified depth to the frac heights at the identified depth to determine whether the produced fluids at the identified depth are primarily contributing hydrocarbons; and k. if produced fluids at the identified depth are not primarily contributing hydrocarbons, taking one or more of the following actions: (i) shutting in the first well; (ii) drilling a second well to a landing zone that avoids the identified depth; or (iii) fracturing multiple stages of a second well without fracturing any stage of the second well at the identified depth.

\* \* \* \* \*